(12) United States Patent  (10) Patent No.: US 9,079,869 B2
List et al.  (45) Date of Patent: Jul. 14, 2015

(54) CHIRAL DISULFONIMIDES

(75) Inventors: Benjamin List, Mülheim an der Ruhr (DE); Frank Lay, Mülheim an der Ruhr (DE); Pilar Garcia Garcia, Salamanca (DE)

(73) Assignee: STUDIENGESELLSCHAFT KOHLE MBH, Muelheim an der Ruhr (DE)

( * ) Notice: Subject to any disclaimer, the term of this patent is extended or adjusted under 35 U.S.C. 154(b) by 116 days.

(21) Appl. No.: 13/203,382

(22) PCT Filed: Mar. 2, 2010

(86) PCT No.: PCT/DE2010/000226
§ 371 (c)(1),
(2), (4) Date: Aug. 25, 2011

(87) PCT Pub. No.: WO2010/099786
PCT Pub. Date: Sep. 10, 2010

(65) Prior Publication Data
US 2011/0313150 A1    Dec. 22, 2011

(30) Foreign Application Priority Data

Mar. 2, 2009 (DE) .......................... 10 2009 011 055

(51) Int. Cl.
*A61K 31/554* (2006.01)
*C07D 285/36* (2006.01)
*C07D 285/01* (2006.01)

(52) U.S. Cl.
CPC .................................... *C07D 285/01* (2013.01)

(58) Field of Classification Search
CPC ............................ A61K 31/554; C07D 285/36
USPC .................. 514/211.1; 540/546, 548; 564/82
See application file for complete search history.

(56) References Cited

U.S. PATENT DOCUMENTS 4,122,088 A    10/1978    Conrow et al.

FOREIGN PATENT DOCUMENTS

| JP | 2005 132815 | 5/2005 |
| JP | 2005 132816 | 5/2005 |
| JP | 2005 134365 | 5/2005 |

OTHER PUBLICATIONS

Farrar, Reactiions of some arenesulphonyl chlorides: Journal of the Chemical Society, Chemical Society, Letchworth; GB, Jul. 1, 1960, pp. 3063-3069.
Garcia-Garcia, "A Powerful Chiral Counteranion Motif for Asymmetric Catalysis", vol. 38, May 13, 2009, pp. 4363-4366.
T Eskow, et al, "Binbam—a new Motif for Strong and Chiral Bronsted Acids"; European Journal of Organic Chemistry, Jun. 17, 2009, pp. 3693-3697.

*Primary Examiner* — Brenda Coleman
(74) *Attorney, Agent, or Firm* — Norris McLaughlin & Marcus, P.A.

(57) ABSTRACT

Chiral disulfonimides having the formula I to III,

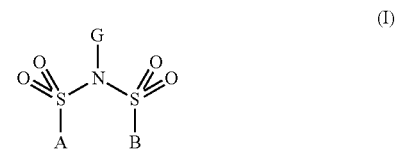

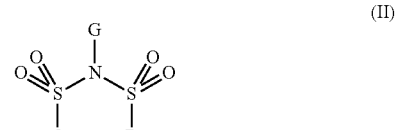

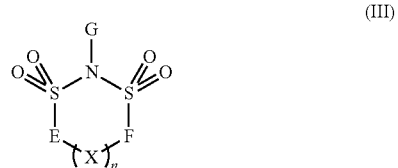

wherein at least one of the groups A and B in the compound of formula I, C and D of the compound in formula II, and E and F of the compound in formula III is a chiral group, or E and F together form a chiral backbone,
X is C, Si, O, N or S, and n is 0, 1, 2, 3, 4, 5 or 6, where n is >1 only if X is C, and
G is as defined herein, and to the organic salts, metal salts and metal complexes thereof, are suited as NMR shift reagents and as reagents for racemate splitting, and also as chiral Brønsted acid catalysts or chiral Lewis acid catalysts for activating ketones, aldehydes and alkenes, and also as catalysts in the organic synthesis.

27 Claims, No Drawings

CHIRAL DISULFONIMIDES

This application is a 371 of International Patent Application No. PCT/DE2010/000226, filed Mar. 2, 2010, which claims priority of German Patent Application No. DE 10 2009 011 055.0, filed Mar. 2, 2009, the contents of both of which patent applications are incorporated herein by reference.

The present invention relates to chiral disulfonimides and also their salts and metal complexes and their use as catalysts.

Many chemical transformations are catalyzed by Brønsted acids. In enantioselective organocatalysis, this possibility of metal-free, and in the case of chiral Brønsted acids also enantioselective, catalysis is a rapidly growing field with increasing applications. In this field of organocatalysis, a distinction is made between hydrogen bond catalysts such as thioureas and also TADDOL and BINOL derivatives and stronger Brønsted acids such as phosphoric diesters and derivatives thereof. However, the possibility of activation by means of these chiral, organic Brønsted acids is restricted to reactive electrophiles such as imines and nitroolefins and also in a few cases to ketones and activated aldehydes. The preparation of very strong, chiral Brønsted acids for activating simple ketones, aldehydes and alkenes is therefore desirable.

In *J. Am. Chem. Soc.* 2006, 128, 9626-9627, Yamamoto et al. introduce chiral, substituted N-triflylphosphoramides as strong Brønsted acids for the activation of ketones. The preparation of a likewise strong, chiral Brønsted acid, viz. 1,1'-binaphthalene-2,2'-disulfonic acid, has been described by Barber and Smiles in *J. Chem. Soc.* 1928, 1141-1149. In *J. Chem. Soc.* 1957, 13-22, Armarego and Turner examined the optical activity and optical stability of this acid. The Japanese patents 2005-132815, 2005-132816 and 2005-134365 disclose the enantiomerically pure preparation of this acid, its use as reagent for resolution of racemates and its use as NMR shift reagent. List et al used this acid as chiral Brønsted acid catalyst in *Adv. Synth. Catal.* 2008, 350, 962-966 and *Chem. Asian. J.* 2008, 3, 430-437, but without achieving enantioselectivity. Ishihara et al. used 1,1'-binaphthalene-2,2'-disulfonic acid in combination with substituted pyridines as chiral Brønsted acid-based organocatalysts in *J. Am. Chem. Soc.* 2008, 130, 16858-16860.

The unknown cyclic disulfonimide of 1,1'-binaphthalene-2,2'-disulfonic acid, its substituted derivatives and the substituted derivatives of 1,1'-binaphthalene-2,2'-disulfonic acid can similarly be classified as strong Brønsted acid. The conjugated bases of the disulfonic acids and disulfonimides are likewise suitable as chiral anions in enantioselective catalysis by counterions and in Lewis acid catalysis.

It was accordingly an object of the present invention to provide chiral disulfonimides and a simple process for preparing chiral disulfonimides and also their use in catalysis.

The present invention accordingly provides chiral disulfonimides having the general formulae I to III

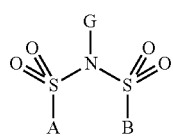
(I)

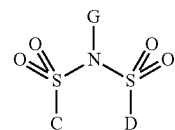
(II)

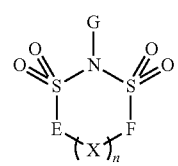
(III)

where at least one of the radicals A and B in the compound of the formula I, C and D of the compound of the formula II and E and F of the compound of the formula III is a chiral radical or E and F together form a chiral backbone, G is H, $C_1$-$C_6$-alkyl, $C_2$-$C_6$-alkenyl or $C_2$-$C_6$-alkynyl, aryl, aryl-($C_1$-$C_6$)-alkyl, hetero($C_1$-$C_6$)-alkyl, heteroaryl, or $SiR^{14}R^{15}R^{16}$, Br, Cl, I, F, where $R^{14}$, $R^{15}$, $R^{16}$ are each $C_1$-$C_6$-alkyl, $C_2$-$C_6$-alkenyl or $C_2$-$C_6$-alkynyl, aryl, aryl-($C_1$-$C_6$)-alkyl, hetero($C_1$-$C_6$)-alkyl, heteroaryl, which may optionally be substituted, X is C, Si, O, N or S and n is 0, 1, 2, 3, 4, 5 or 6, where n is >1 only when X is C, and also their organic salts, metal salts and metal complexes.

The compounds having the formulae I, II and III can also be summarized by the general formula Z

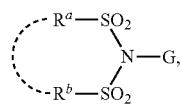
Z

One of $R^a$ and $R^b$ or both is/are chiral radicals as for the radicals A, B, C, D, E and F or they together form a chiral backbone and G is H, $C_1$-$C_6$-alkyl, $C_2$-$C_6$-alkenyl or $C_2$-$C_6$-alkynyl, aryl, aryl-($C_1$-$C_6$)-alkyl, hetero($C_1$-$C_6$)-alkyl, heteroaryl, or $SiR^{14}R^{15}R^{16}$, Br, Cl, I, F, where $R^{14}$, $R^{15}$, $R^{16}$ are each $C_1$-$C_6$-alkyl, $C_2$-$C_6$-alkenyl or $C_2$-$C_6$-alkynyl, aryl, aryl-($C_1$-$C_6$)-alkyl, hetero($C_1$-$C_6$)-alkyl, heteroaryl, which may optionally be substituted.

In the compounds which are derived from TADDOL (17+18 in the examples), BINOL (1-3, 21+22) and VAPOL (4) and in the case of the spiro compound (19), the radicals E and F together form a chiral backbone. The chirality in the compounds derived from BINOL and VAPOL and the spiro compounds results from axial chirality. In this type of chirality, the rotation about the axis of the aryl(E)-aryl(F) bond (X) is limited. The two aryls are not themselves chiral, but by means of the connection via an axis about which free rotation is limited they together form a chiral axis. This results in a chiral backbone for the disulfonimides. The compound having the formula Z and the compounds having the formulae I, II and III can also have a helical, chiral or planar backbone, for example compound 24.

For the purposes of the present invention, "chiral sulfonimides" means that one of the enantiomers is present in excess, i.e. the compound is enriched in the one enantiomer, or the reaction product is present in enantiomerically pure form. If the compounds according to the invention are obtained as a racemic or scalemic mixture as reaction product, the enantiomers can be separated by means of methods which are well known from the prior art, for example by separation by means of chiral, preparative HPLC or by reaction of the compounds with chiral agents and subsequent separation of the diastereomers. The enantiomers can also be separated when the mixture is to be enriched further in the enantiomer present in excess, i.e. the ee is to be increased.

Any chiral radicals are possible as chiral radicals. If the other radical in each case is not chiral, the radicals A or B, C or D and E or F are any organic radical which may be saturated or unsaturated, linear, cyclic or heterocyclic, aromatic and/or heteroaromatic. Examples of compounds having the formulae I, II and III are shown below:

1
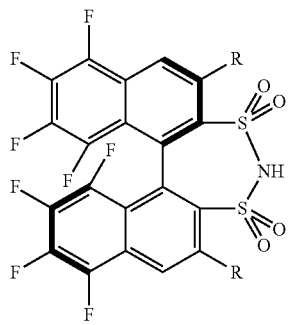

2
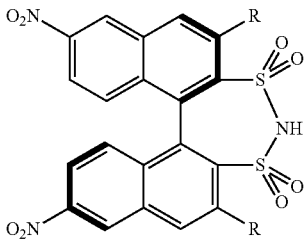

3
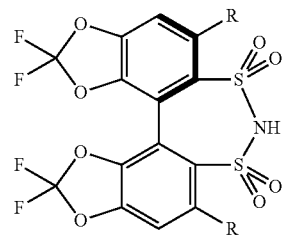

4
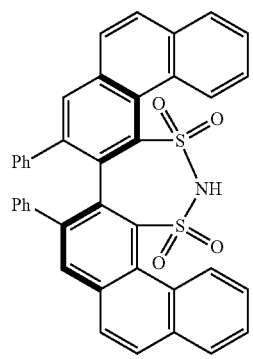

-continued

5
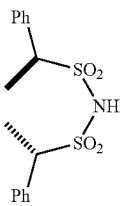

6
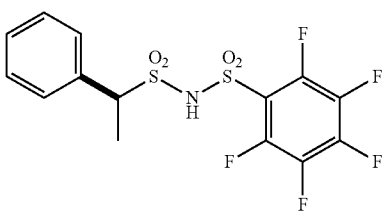

7
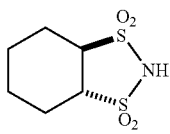

8
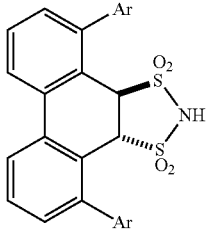

9
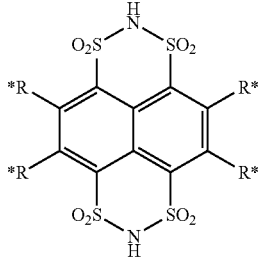

10
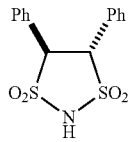

11
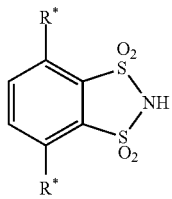

12
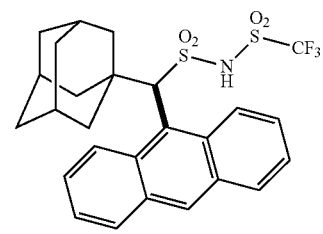
13
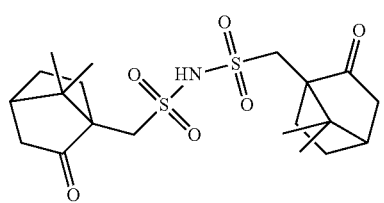
14
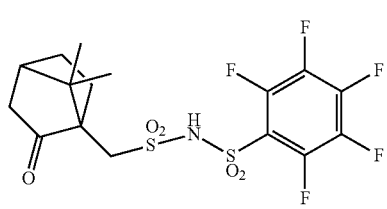
15
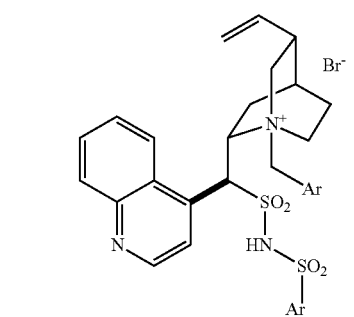
16
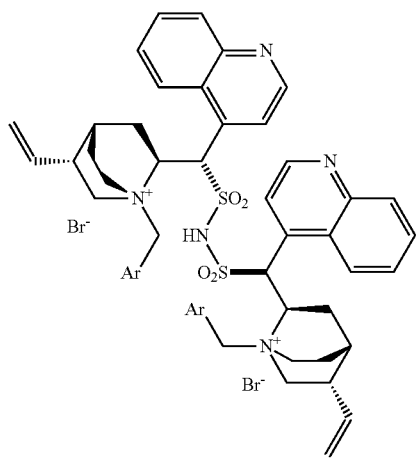
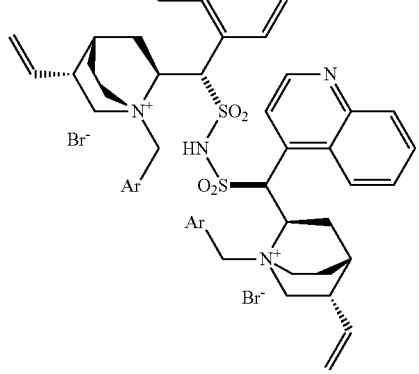
17
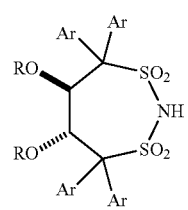
18
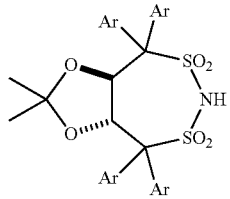
19
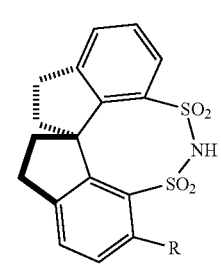
20
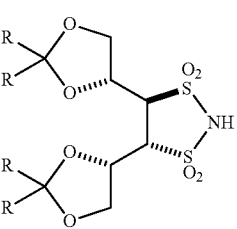
21
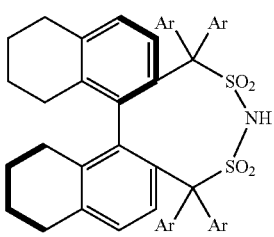
22
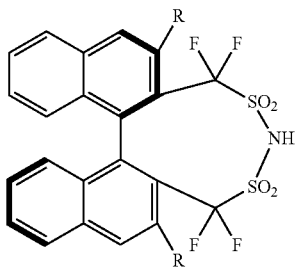
23
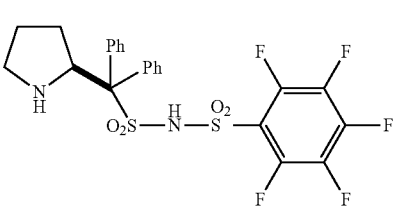

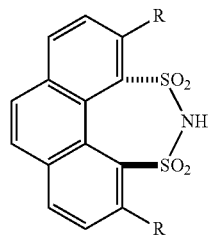

In organic synthesis, particularly in the synthesis of pharmaceutical active compounds, chiral compounds are frequently used as catalysts in order to obtain the desired product in a high enantiomeric purity or diastereomeric purity. Compounds in which the radicals in the compounds of the formulae I to III are derived from BINOL have been found to be particularly suitable for use as catalysts in organic synthesis. These preferred compounds are represented by the general formula IV

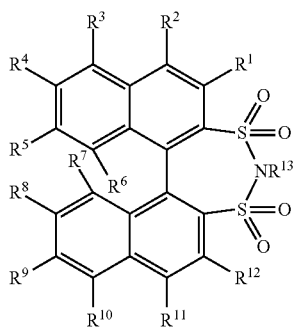

where $R^1$, $R^2$, $R^3$, $R^4$, $R^5$, $R^6$, $R^7$, $R^8$, $R^9$, $R^{10}$, $R^{11}$ and $R^{12}$ can be identical or different and are each, independently of one another, H, OH, F, Cl, Br, I, CN, $NO_2$, NO, $SO_2$, $SO_3H$, $NH_2$, $PH_3$, COOH, $SO_3X$, COOY, where X and Y are each Na or K, a $C_1$-$C_{20}$-alkyl, $C_2$-$C_{20}$-alkenyl or $C_2$-$C_{20}$-alkynyl, aryl, aryl-($C_1$-$C_6$)-alkyl, hetero($C_1$-$C_6$)-alkyl, heteroaryl group, which may optionally be substituted, $R^{13}$ is H, $C_1$-$C_6$-alkyl, $C_2$-$C_6$-alkenyl or $C_2$-$C_6$-alkynyl, aryl, aryl-($C_1$-$C_6$)-alkyl, hetero($C_1$-$C_6$)-alkyl, heteroaryl, or $SiR^{14}R^{15}R^{16}$, Br, Cl, I, F, where $R^{14}$, $R^{15}$, $R^{16}$ are each $C_1$-$C_6$-alkyl, $C_2$-$C_6$-alkenyl or $C_2$-$C_6$-alkynyl, aryl, aryl-($C_1$-$C_6$)-alkyl, hetero($C_1$-$C_6$)-alkyl, heteroaryl, which may optionally be substituted, and also their organic salts, metal salts and metal complexes.

The present invention further provides chiral disulfonimides derived from H8-BINOL having the general formula V

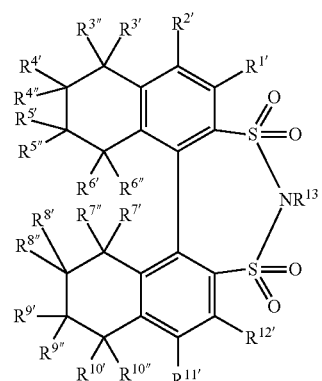

where $R^{1'}$, $R^{2'}$, $R^{3''}$, $R^{3'}$, $R^{4'}$, $R^{4''}$, $R^{5'}$, $R^{5''}$, $R^{6'}$, $R^{6''}$, $R^{7'}$, $R^{7''}$, $R^{8'}$, $R^{8''}$, $R^{9'}$, $R^{9''}$, $R^{10'}$, $R^{10''}$, $R^{11'}$ and $R^{12'}$ can be identical or different and are each, independently of one another, H, OH, F, Cl, Br, I, CN, $NO_2$, NO, $SO_2$, $SO_3H$, $NH_2$, $PH_3$, COOH, $SO_3X$, COOY, where X and Y are each Na or K, a $C_1$-$C_{20}$-alkyl, $C_2$-$C_{20}$-alkenyl or $C_2$-$C_{20}$-alkynyl, group, aryl, aryl-($C_1$-$C_6$)-alkyl, hetero($C_1$-$C_6$)-alkyl, heteroaryl, which may optionally be substituted, $R^{13}$ is H, $C_1$-$C_6$-alkyl, $C_2$-$C_6$-alkenyl or $C_2$-$C_6$-alkynyl, aryl, aryl-($C_1$-$C_6$)-alkyl, hetero($C_1$-$C_6$)-alkyl, heteroaryl, or $SiR^{14}R^{15}R^{16}$, Br, Cl, I, F, where $R^{14}$, $R^{15}$, $R^{16}$ are each $C_1$-$C_6$-alkyl, $C_2$-$C_6$-alkenyl or $C_2$-$C_6$-alkynyl, aryl, aryl-($C_1$-$C_6$)-alkyl, hetero($C_1$-$C_6$)-alkyl, heteroaryl, which may optionally be substituted, and also their organic salts, metal salts and metal complexes.

A further preferred embodiment provides compounds having the following general formulae VI, VII, VIII and IX

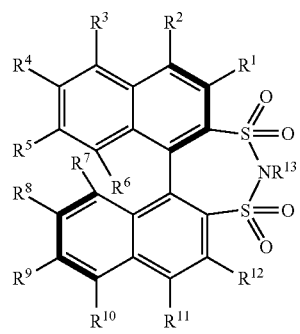

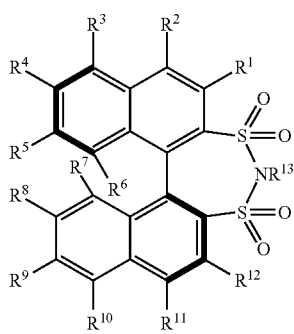

-continued

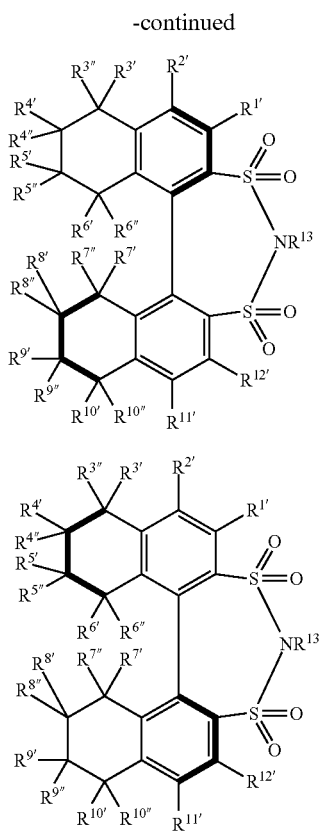

(VIII)

(IX)

where the radicals $R^1, R^2, R^3, R^4, R^5, R^6, R^7, R^8, R^9, R^{10}, R^{11}$ and $R^{12}, R^{1'}, R^{2'}, R^{3'}, R^{3''}, R^{4'}, R^{4''}, R^{5'}, R^{5''}, R^{6'}, R^{6''}, R^{7'}, R^{7''}, R^{8'}, R^{8''}, R^{9'}, R^{9''}, R^{10'}, R^{10''}, R^{11'}$ and $R^{12'}$ and also $R^{13}$ are as defined above, where the enantiomers are present in a ratio of from 98:2 to 100:0, i.e. in enantiomerically pure form.

It has been found that the compounds according to the invention are well suited as catalysts for enantioselective synthesis. Here, they function as chiral Brønsted acids or in the case of $R^{13}$=$SiR^{14}R^{15}R^{16}$ as Lewis acids or the conjugated base thereof as chiral anions in enantioselective catalyses by counterions.

The following definitions for the individual radicals $R^1, R^2, R^3, R^4, R^5, R^6, R^7, R^8, R^9, R^{10}, R^{11}$ and $R^{12}$ apply equally to the radicals $R^{1'}, R^{2'}, R^{3'}, R^{3''}, R^{4'}, R^{4''}, R^{5'}, R^{5''}, R^{6'}, R^{6''}, R^{7'}, R^{7''}, R^{8'}, R^{8''}, R^{9'}, R^{9''}, R^{10'}, R^{10''}, R^{11'}$ and $R^{12'}$ and the radical $R^{13}$.

$C_1$-$C_{20}$-Alkyl can be unbranched (linear) or branched and has 1, 2, 3, 4, 5, 6, 7, 8, 9, 10, 11, 12, 13, 14, 15, 16, 17, 18, 19 or 20 carbon atoms. Alkyl is preferably $C_1$-$C_6$-alkyl, in particular methyl, ethyl, propyl, isopropyl, butyl, isobutyl, sec-butyl or tert-butyl, likewise pentyl, 1-, 2- or 3-methylpropyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Preferred substituted alkyl radicals are trifluoromethyl, pentafluoroethyl and 1,1,1-trifluoroethyl.

Cycloalkyl is preferably cyclopropyl, cyclobutyl, cyclopentyl, cyclohexyl or cycloheptyl. Alkylene is preferably methylene, ethylene, propylene, butylene, pentylene or hexylene, but also branched alkylene.

Alkenyl is preferably vinyl.
Alkynyl is preferably C≡CH.
Halogen is F, Cl, Br or I.

Alkoxy is preferably methoxy, ethoxy, propoxy or butoxy.

$C_3$-$C_8$-Heterocycloalkyl having one or more heteroatoms selected from among N, O and S is preferably 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Optionally substituted means unsubstituted or monosubstituted, disubstituted, trisubstituted, tetrasubstituted or pentasubstituted.

Aryl is preferably phenyl, naphthyl or biphenyl.
Arylalkyl is preferably benzyl.

Heteroaryl having one or more heteroatoms selected from among N, O and S is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-Indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, also preferably 1,3-benzodioxol-5-yl, 1,4-benzodioxan-6-yl, 2,1,3-benzothiadiazol-4- or -5-yl or 2,1,3-benzoxadiazol-5-yl.

In a preferred embodiment of the present invention, at least one of $R^1$ and $R^{12}$ or $R^{1'}$ and $R^{12'}$ is not hydrogen and is selected from among phenyl-, 2,4,6-triisopropylphenyl, mesityl, 9-phenanthryl, 9-anthracenyl, ferrocenyl, N-(perfluorophenyl)acetamide, N-(4-chlorophenyl)acetamide, N-(naphthalen-1-yl)acetamide, N-benzhydrylacetamide, N-(2,6-diisopropylphenyl)acetamide, 1-anthracenyl, corannulene, porphyrin, 1-naphthyl, 2-naphthyl, 4-biphenyl, 3,5-(trifluoromethyl)phenyl, 2,6-dimethylphenyl, tert-butyl, trismesitylsilyl, tris-phenylsilyl, 4-nitrophenyl and 2,6-methyl-4-butylphenyl, trifluoromethyl, unbranched (linear) and branched ($C_1$-$C_{12}$)-perfluoroalkyls, 3,4,5-trifluorophenyl, 1,3-bis(perfluoropropan-2-yl)phenyl, 1,3-bis(perfluorobutyl)phenyl and/or pentafluorophenyl and also chloride, iodide, fluoride, $B(OH)_2$, $B(alkyl)_2$, $B(Oalkyl)_2$, $B(pinacol)$, $BF_3X$ where X=Na or K, OTf, MgCl, MgBr, ZnCl. The other radicals are preferably hydrogen.

In a further preferred embodiment of the present invention, at least one of the radicals $R^4$ and $R^9$ or $R^{4'}, R^{4''}, R^{9'}$ and $R^{9''}$ is selected from among $NO_2$ and I.

The compounds according to the invention can be converted in process steps which are well known per se to those skilled in the art into organic salts, metal salts or metal complexes. In one possible embodiment, the disulfonimides are reacted with an appropriate metal salt, for example with the carbonate of the appropriate metal.

Examples of organic salts, metal salts and metal complexes are shown in the following scheme:

metal compounds or complexes. Suitable metal compounds are derived from Li, Na, K, Rb, Cs, Be, Mg, Ca, Sr, Ba Sc, Ti, V, Cr, Mn, Fe, Co, Ni, Cu, Zn, Y, Zr, Mo, Ru, Rh, Pd, Ag, W, Re, Os, Ir, Pt, Au, Al, Pb, La, Sm, Eu, Yb.

Scheme 1: General examples of metal salts and metal complexes of the disulfonimides IV and disulfonimides V.

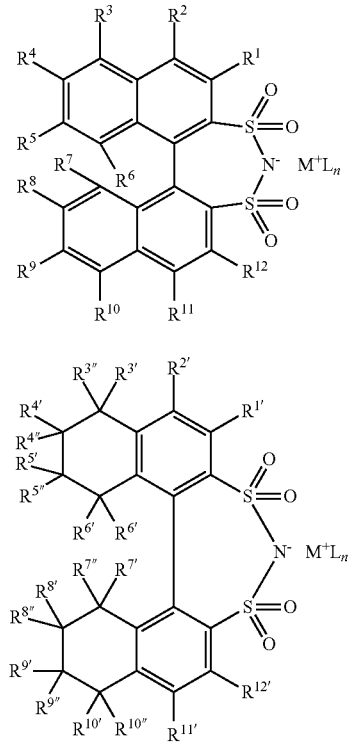

Scheme 2: Examples of possible cations.

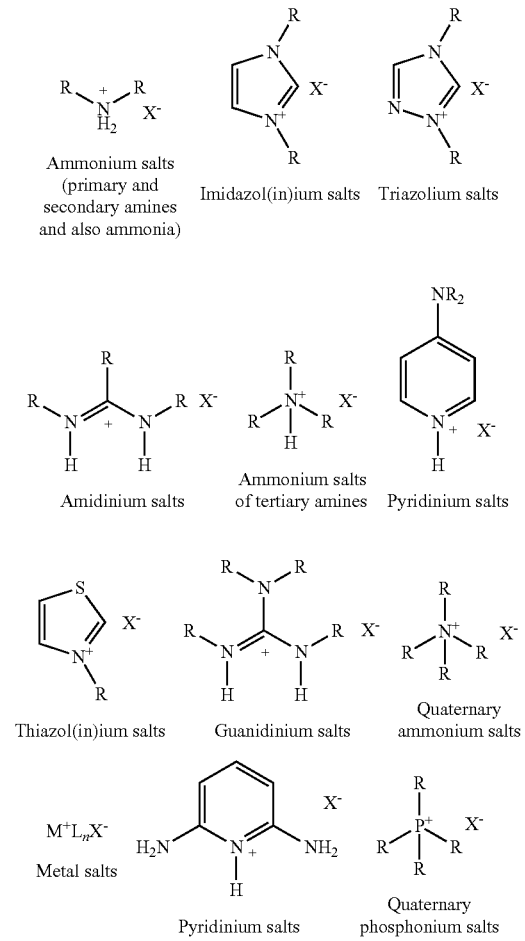

In scheme 1, any metals or organic cations, e.g. tertiary ammonium ions, can be represented by M. L refers to any ligands present in the number n=0-10. Even though the compounds are shown as salts in scheme 1, the precise structure with metals is not known; they can also have the structure of metal complexes. The formulation metal salts or metal complexes is therefore used for the purposes of the present invention. The metal compounds are not restricted to particular Examples of Synthetic Routes in which A and/or B, C and/or D and Also E and/or F are Chiral Aliphatic Radicals:

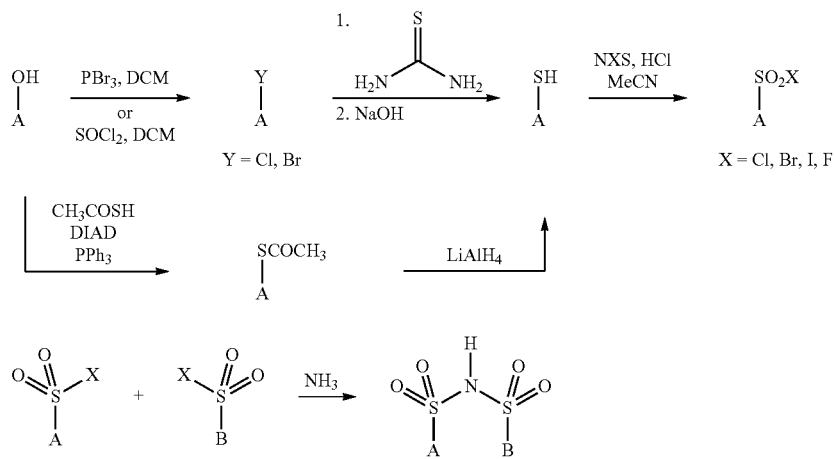

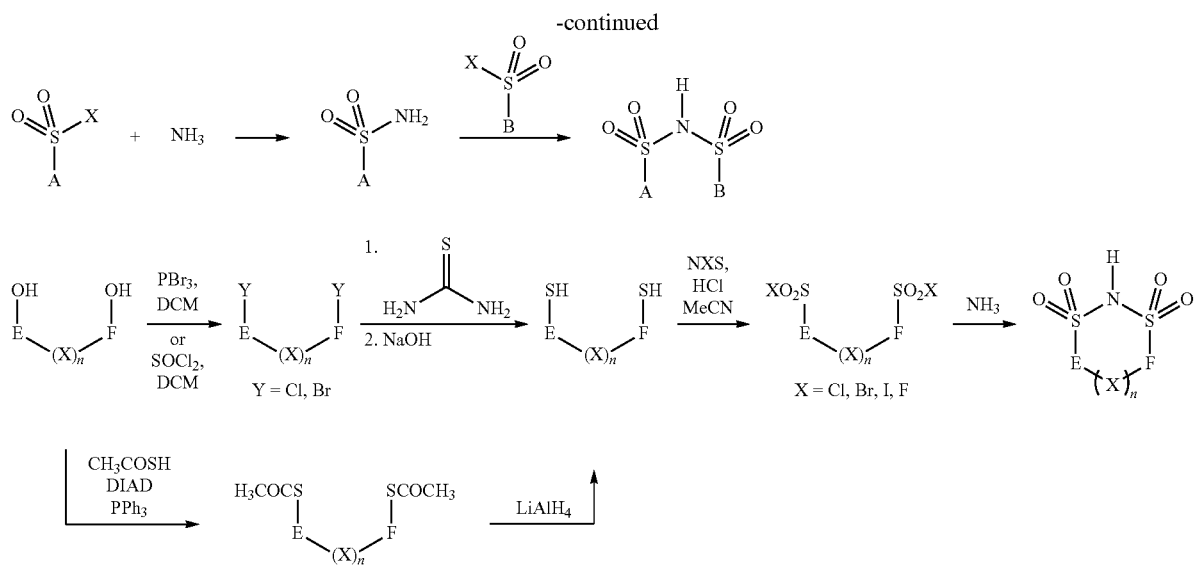

If A, B, C, D, E, F are aromatic radicals, the synthesis can be carried out via a Newman-Kwart rearrangement:

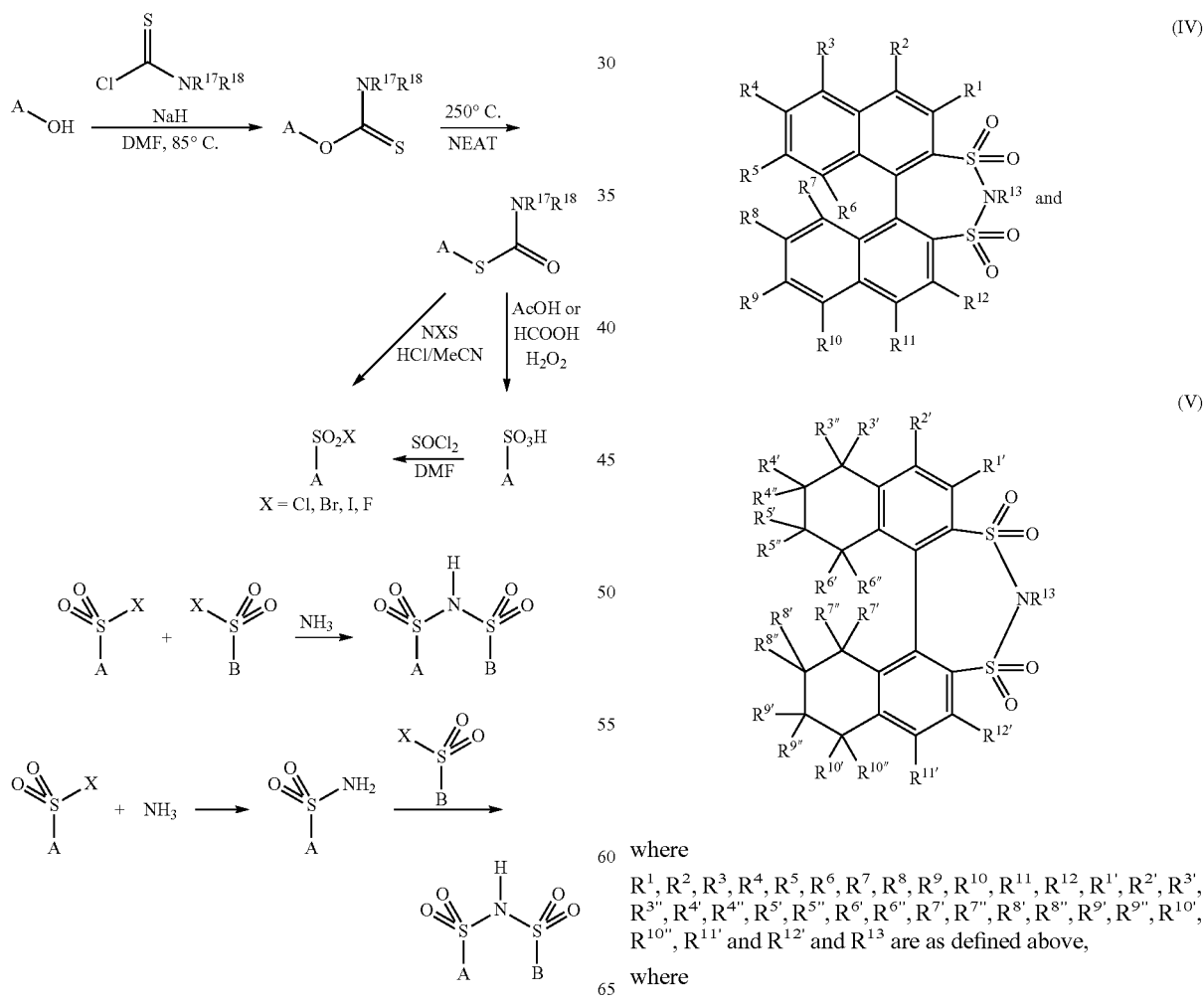

A preferred preparative process of the present invention is a process for preparing substituted disulfonimides having the general formula I or II, i.e. disulfonimides having a chiral BINOL and H8 BINOL backbone:

where
$R^1, R^2, R^3, R^4, R^5, R^6, R^7, R^8, R^9, R^{10}, R^{11}, R^{12}, R^{1'}, R^{2'}, R^{3'}, R^{3''}, R^{4'}, R^{4''}, R^{5'}, R^{5''}, R^{6'}, R^{6''}, R^{7'}, R^{7''}, R^{8'}, R^{8''}, R^{9'}, R^{9''}, R^{10'}, R^{10''}, R^{11'}$ and $R^{12'}$ and $R^{13}$ are as defined above, where (A) is a Binol derivative having the general formula X or an H8-Binol derivative having the general formula XI (X)

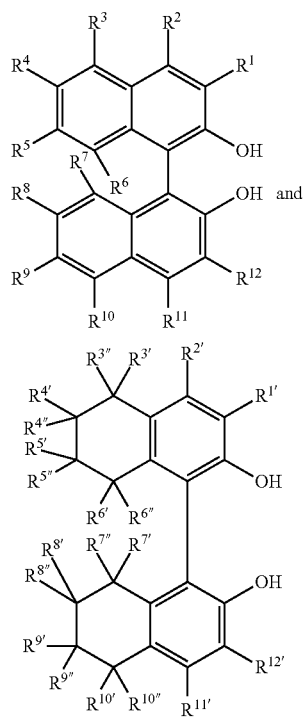

and (XI)

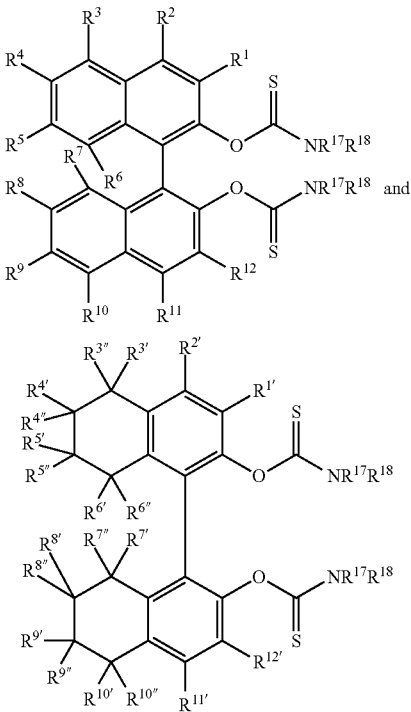

is reacted with a thiocarbamoyl chloride of the general formula XII (XII)

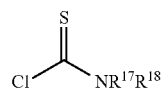

where $R^{17}$ and $R^{18}$ can be identical or different and are each a $C_1$-$C_6$-alkyl group, to form an O-arylthiocarbamate having the general formula XIII or XIV, (XIII)

(XIV)

(B) the O-arylthiocarbamate having the formula XII is converted into the corresponding S-arylthiocarbamate having the formula XV or XVI, (XV)

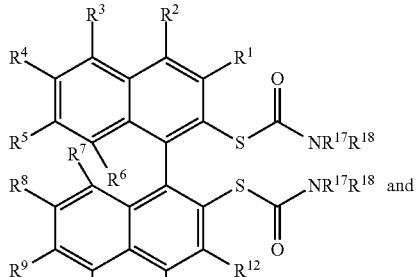

and (XVI)

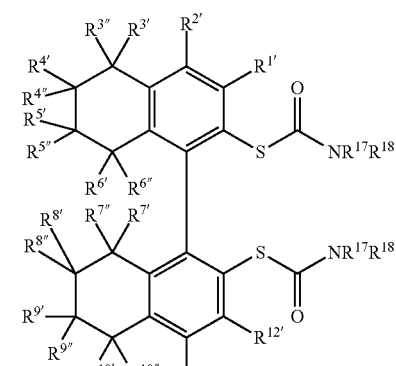

and (C) the S-arylthiocarbamate is converted in the presence of an oxidant into the compounds having the formula XVII or XVIII.

(XVII)

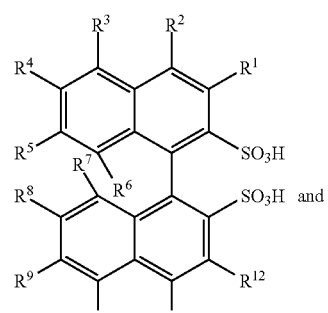

and (XVIII)

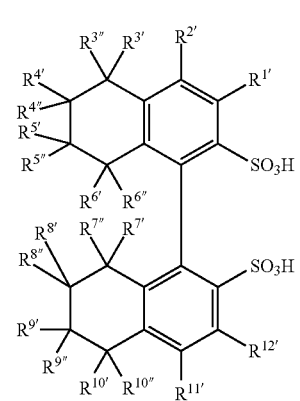

In a process step (D), the sulfonic acids having the formula (VI) are converted in a manner known per se into the acid halides having the formula XIX or XX, where $R^{19}$=Cl, Br, I or F,

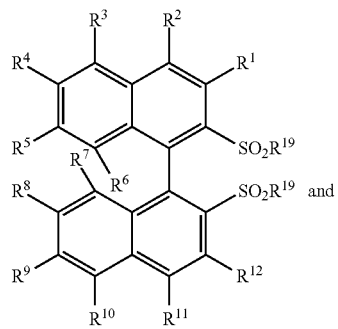

(XIX)

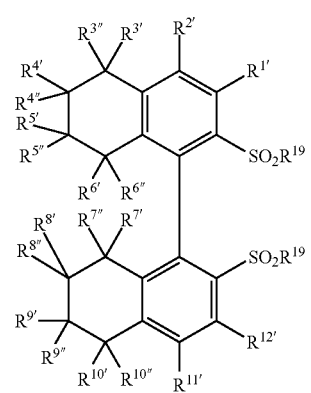

(XX)

and in a subsequent process step (E) are subsequently converted by means of ammonia or a primary amine into the corresponding imide having the formula IV or V.

As an alternative, the S-arylthiocarbamate having the formula XV or XVI can in this synthetic route be converted directly into the acid halides having the formula XIX or XX, where $R^{19}$=Cl, Br, I or F, in a process step (D1) known to those skilled in the art.

An alternative synthetic route starts out from a 3,3'-unsubstituted disulfonimide having the general formula IVa or Va ($R^1$, $R^{12}$=H or $R^{1'}$, $R^{12'}$=H), which can be prepared by the above synthetic route.

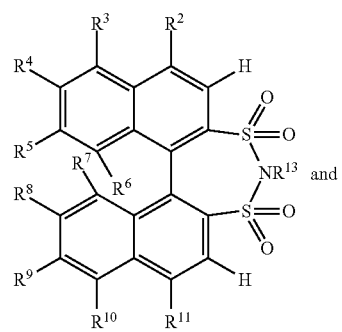

(IVa)

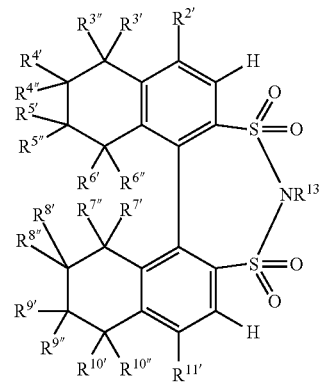

(Va)

This is converted in a process step F) known to those skilled in the art into a 3,3'-dihalide ($R^1$, $R^{12}$=Cl, Br, I or F or $R^{1'}$, $R^{12'}$=Cl, Br, I or F) or a 3,3'-ditriflate ($R^1$, $R^{12}$=OTf or $R^{1'}$, $R^{12'}$=OTf) having the general formula XX or XXI.

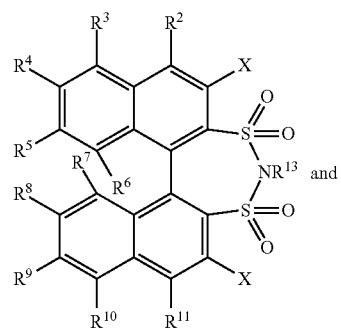

(XX)

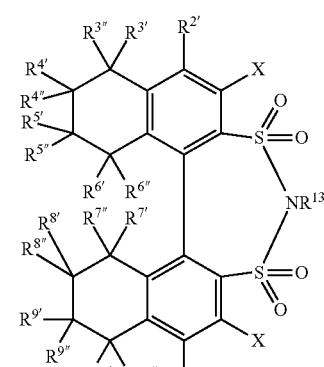

(XXI)

X = Cl, Br, I, F or OTf

As an alternative, the disulfonimides IVa or Va can be converted in this synthetic route into a 3,3'-diboronate ($R^1$, $R^{12}$=B(OH)$_2$, B(alkyl)$_2$, B(Oalkyl)$_2$, B(pinacol), BF$_3$X X=Na, K or $R^{1'}$, $R^{12'}$=B(OH)$_2$, B(alkyl)$_2$, B(Oalkyl)$_2$, B(pinacol), BF$_3$X where X=Na, K) having the general formula XXiiII or XXIII in a process step G) known to those skilled in the art.

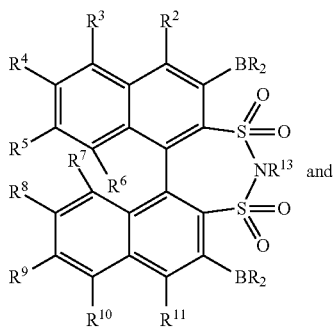

(XXII)

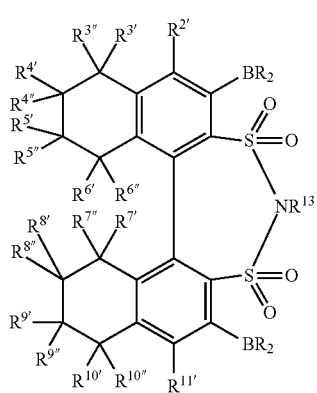

(XXIII)

The halides and ditriflates having the general formula XX or XXI or the boronates having the general formula XXII or XXIII serve as starting substances for the coupling reactions well known to those skilled in the art as process step H) to give the imides having the formula IV or V.

The individual reaction steps of the process of the invention are processes known from the prior art. In process step SA, the dihydroxy compound having the formula IV or V is reacted with a thiocarbamoyl chloride of the formula XII in the presence of a hydride in a solvent at elevated temperatures. Possible solvents are all organic solvents which do not have an adverse effect on the reaction.

The reaction step B is preferably carried out in a suitable solvent or in the absence of solvent by heating the O-arylthiocarbamate obtained in step A. The S-arylthiocarbamate having the formula XV or XVI obtained is converted in the next process step C into a sulfonic acid having the formula XVII or XVIII. This process step is preferably carried out in the presence of an oxidant such as $H_2O_2$ and an acid and/or an organic peracid.

The conversion of the sulfonic acid having the formula XVII or XVIII into the acid imide having the formula IV or V can be carried out in a manner known per se using process steps which are well known to those skilled in the art.

As an alternative, the S-arylthiocarbamate having the formula XV or XVI can be converted directly in the synthetic route into the acid halides having the formula XVII or XVIII, where $R^{19}$=Cl, Br, I or F, in a process step (D1) known to those skilled in the art.

An example of a general synthetic route from BINOL X to disulfonimide IV is shown in scheme 3. The synthetic route for disulfonimide V is analogous and starts out from an H8-BINOL XI (scheme 4). Starting substances are corresponding substituted or unsubstituted BINOLs X or H8-BINOLs XI, and these are converted by means of dimethylthiocarbamoyl chloride into the corresponding O-arylthiocarbamate XIII or XIV. A Newman-Kwart rearrangement gives the S-arylthiocarbamate XV or XVI which is converted under oxidative conditions into the disulfonic acid XVII or XVIII. Conversion of this acid into the corresponding sulfonic acid halides XIX or XX and ring closure by means of ammonia give the disulfonimide IV or V.

As an alternative, the S-arylthiocarbamate having the formula XV or XVI can be converted directly in this synthetic route into the acid halides having the formula XIX or XX in a process step (D1) known to those skilled in the art. Ring closure by means of ammonia gives the disulfonimide IV or V. A general description of the preparation of the disulfonimides is given in the experimental part.

Scheme 3. Synthetic route according to the invention to disulfonimide IV.

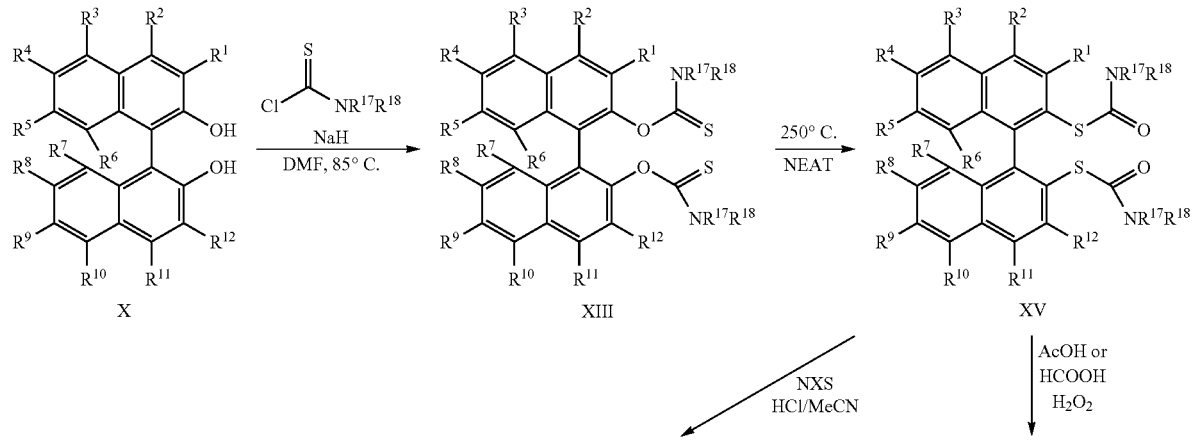

-continued

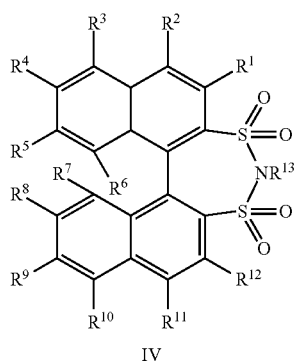

IV

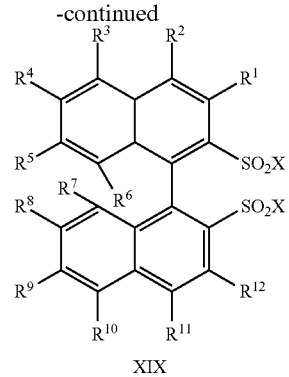

XIX $R^{19} = X = Cl, Br, I, F$

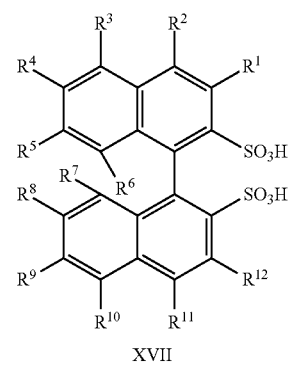

XVII

Scheme 4. Synthetic route according to the invention to disulfonimide V.

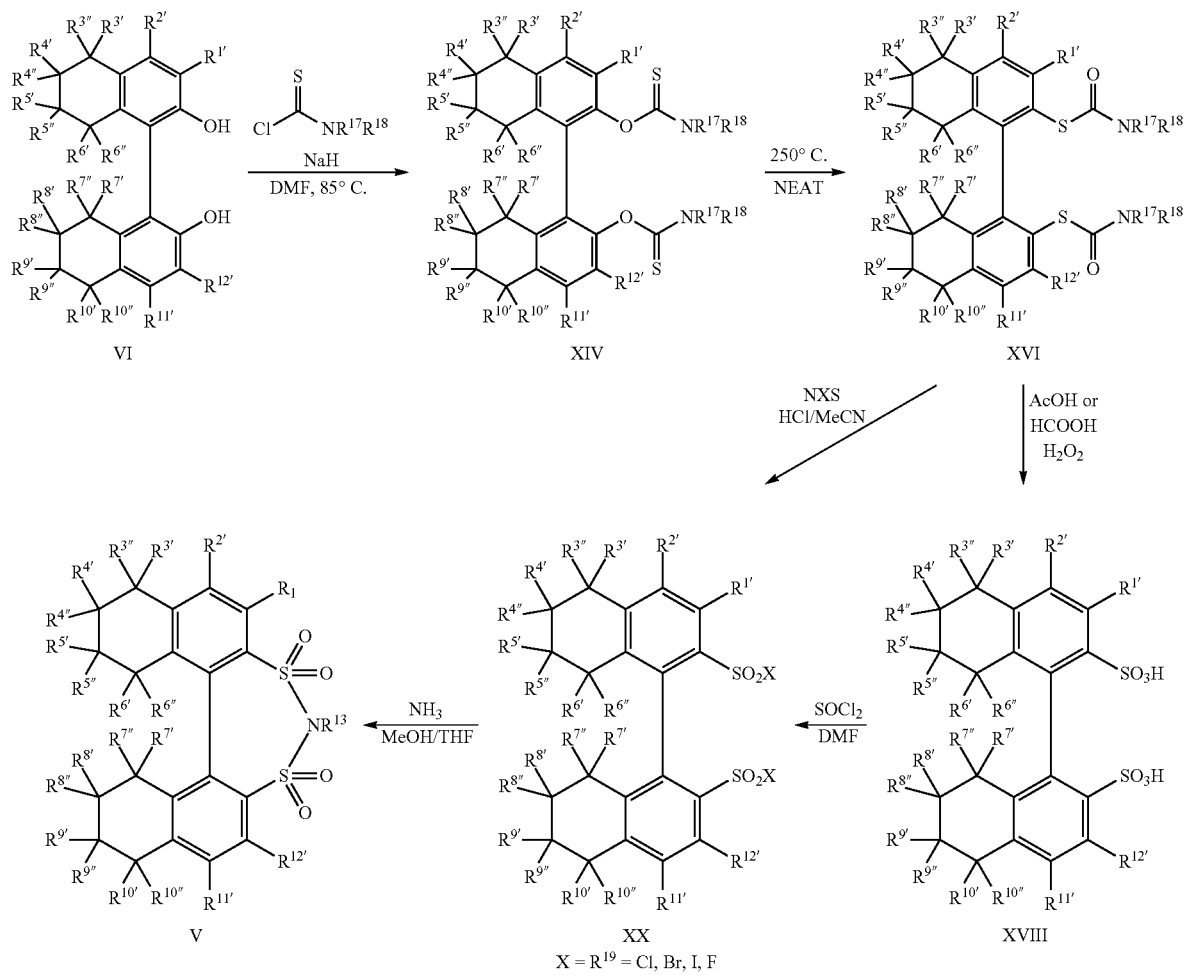

$X = R^{19} = Cl, Br, I, F$

In an alternative synthetic route, the disulfonimides IVa or Va prepared by the above route ($R^1$, $R^{12}$=H or $R^{1'}$, $R^{12'}$=H) serve as starting substances. The disulfonimides IVa or Va are converted by means of a process step which is well known to those skilled in the art into the halides or ditriflates having the general formula XX or XXI or the boronates having the general formula XXII or XXIII. These serve as starting substances for coupling reactions to form the imides having the formula IV or V. Variation of $R^1$, $R^{12}$ or $R^{1'}$, $R^{12'}$ via the disulfonimides IVa or Va is also possible by not quenching the metal species formed in situ by means of a directing ortho-metallization ($R^1$, $R^{12}$=Li, Mg, Zn, Cu or $R^{1'}$, $R^{12'}$=Li, Mg, Zn, Cu) with halogen sources but rather with other, suitable electrophiles such as $CO_2$, perfluoroalkyl iodides or isocyanates, aldehydes or ketones.

Scheme 5.
Synthetic routes according to the invention to disulfonimide IV via disulfonimide IVa
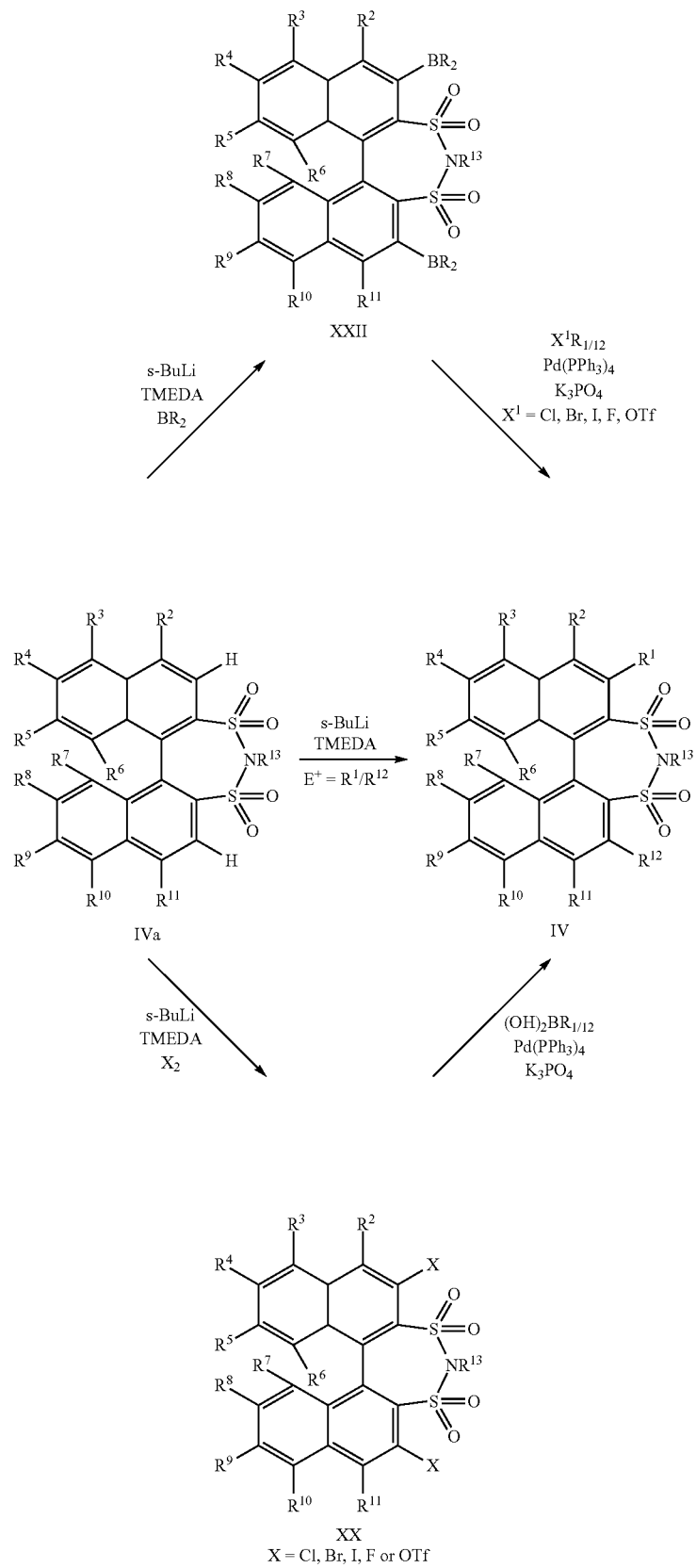

Scheme 6.
Synthetic routes according to the invention to disulfonimide V via disulfonimide Va.
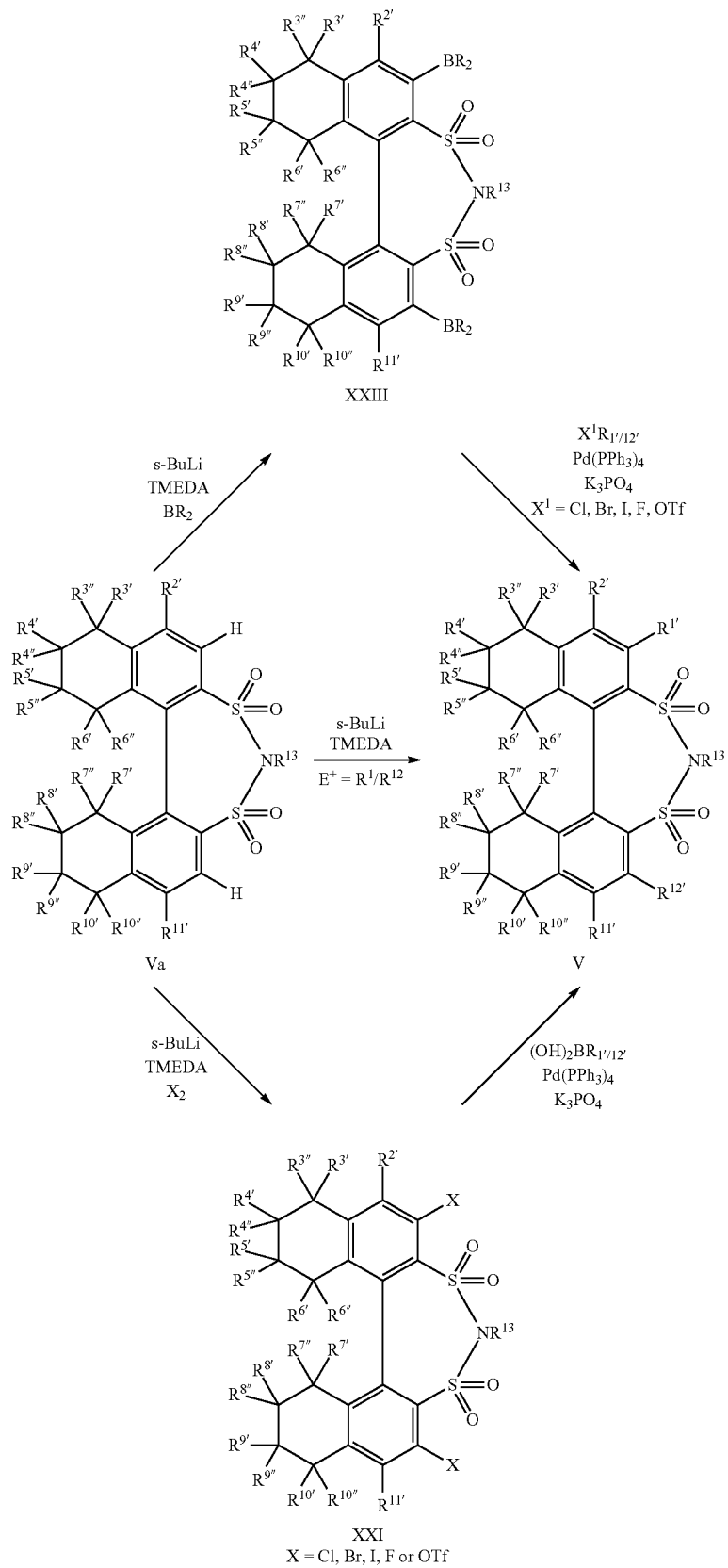

Use as Catalysts

The disulfonimides I-III of the invention and their organic salts, metal salts and metal complexes are particularly suitable as strong, chiral Brønsted acid catalysts or chiral Lewis acid catalysts for many reactions, in particular for the activation of ketones, aldehydes and alkenes. A particularly good catalytic activity is displayed by compounds in which $R^{13}$ is H, F, Cl, Br, I or $SiR^{14}R^{15}R^{16}$, where $R^{14}$, $R^{15}$, $R^{16}$ are each $C_1$-$C_6$-alkyl, $C_2$-$C_6$-alkenyl or $C_2$-$C_6$-alkynyl. $R^{13}$ is particularly $SiR^{14}R^{15}R^{16}$ or I.

The reactions in which the compounds according to the invention can be used as catalysts include reactions such as aldol reactions, vinylic aldol reactions, Mukaiyama aldol reactions, vinylic Mukaiyama aldol reactions, Mukaiyama-Michael reactions, Michael additions, Mannich reactions, TMSCN additions onto aldehydes and ketones, esterifications, etherifications, pinacol rearrangements, as acetalizations and related reactions, cycloadditions, hydroaminations, hydroalkoxylation, hydrations, olefin activations in general, Friedel-Crafts reactions, epoxide openings, Ritter reactions, nucleophilic substitutions of alcohols, asymmetric ring openings, asymmetric reductions, transfer hydrogenations, alkyne additions, allylations, epoxidations, olefin metathesis, isomerizations, iminium catalysis and enamine catalysis.

A selection of these reactions is shown in schemes 7 and 8.

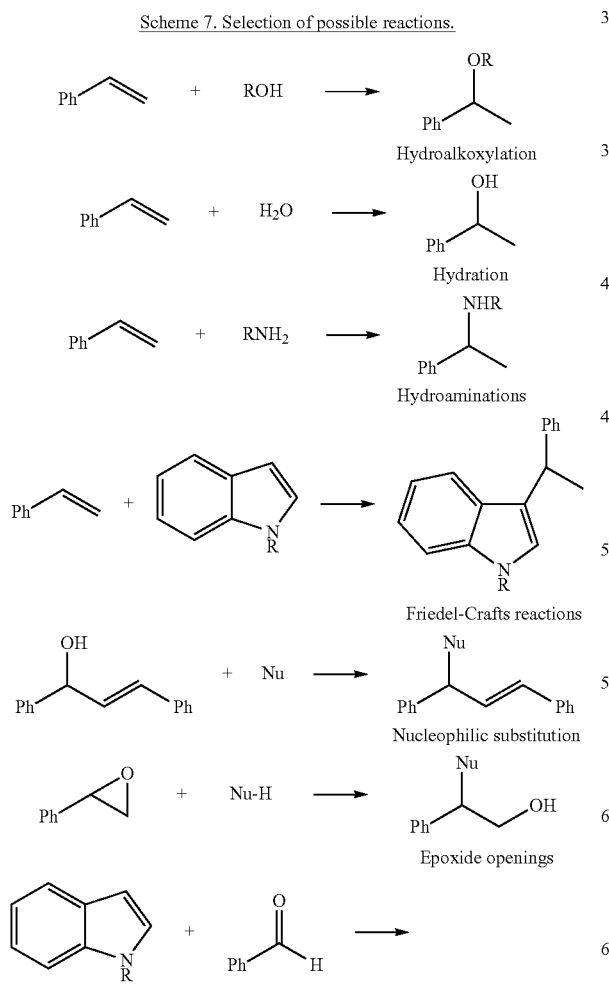

Scheme 7. Selection of possible reactions.

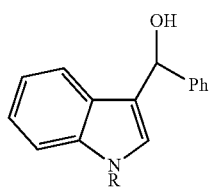

Friedel-Crafts reactions

Scheme 8. Selection of possible reactions.

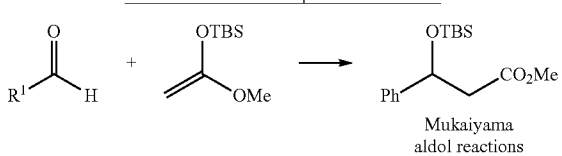

Mukaiyama aldol reactions

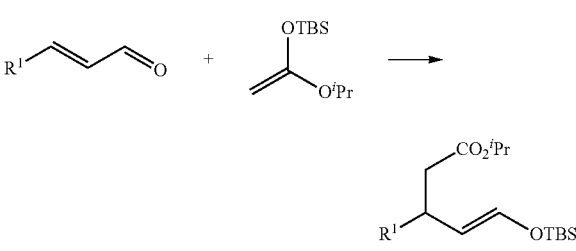

Mukaiyama-Michael addition

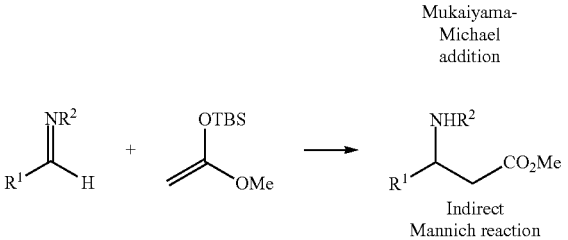

Indirect Mannich reaction

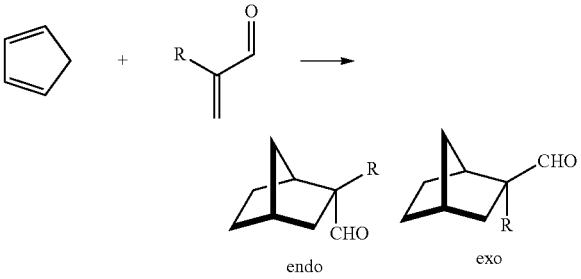

Diels-Alder reaction

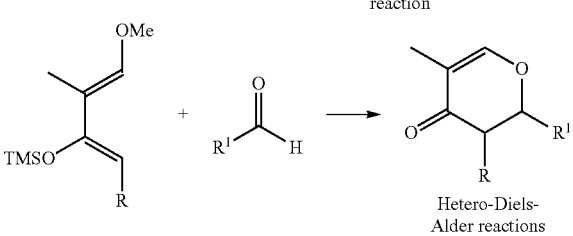

Hetero-Diels-Alder reactions

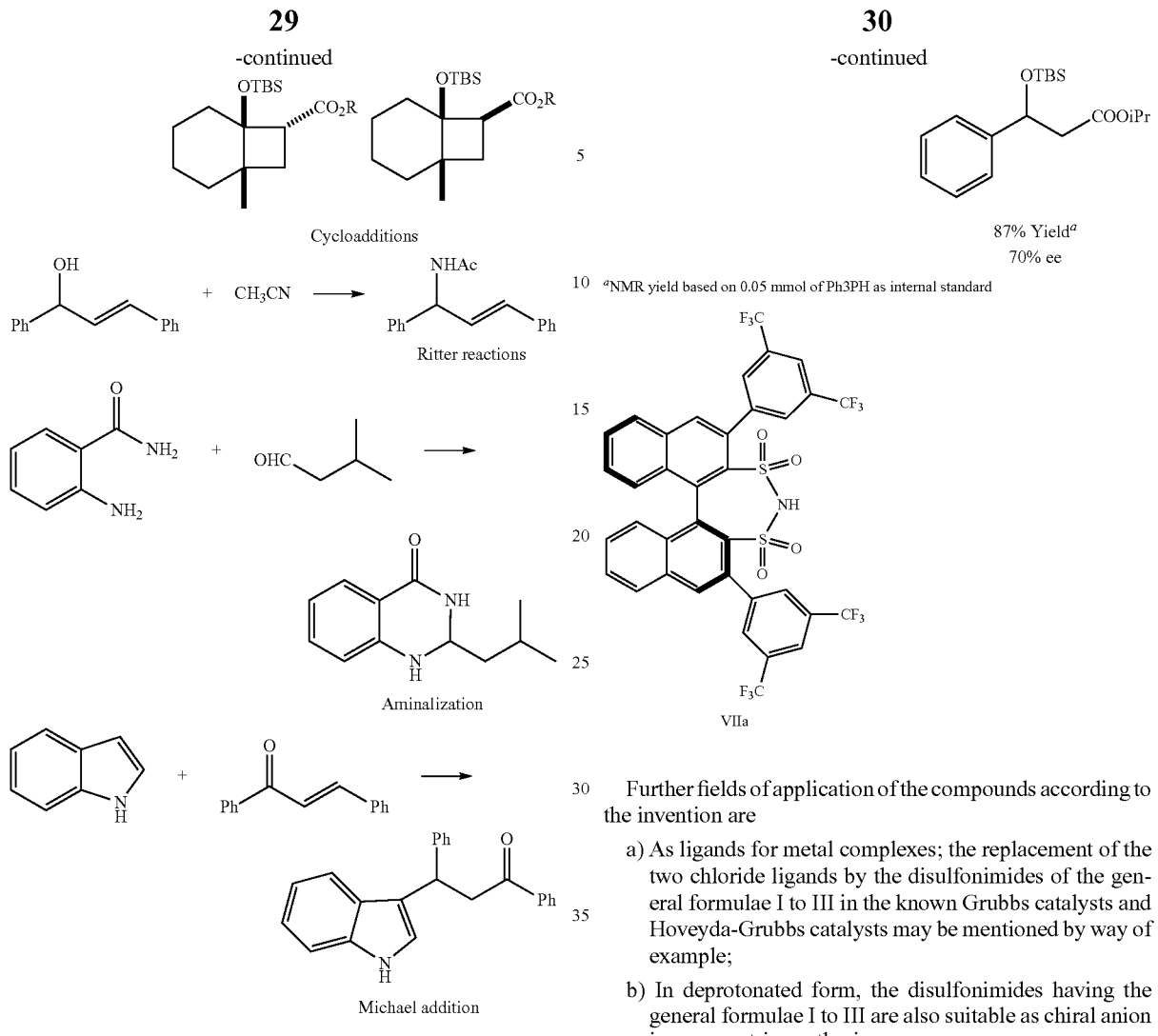

First results achieved in the Mukaiyama aldol reaction using disulfonimide VIIa are shown by way of example in scheme 9.

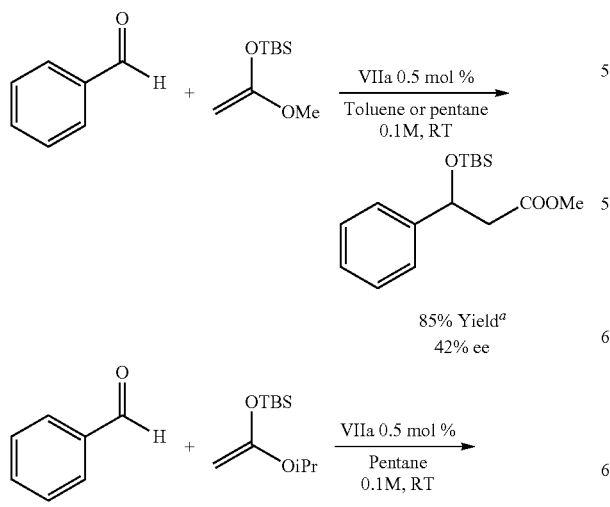

Further fields of application of the compounds according to the invention are a) As ligands for metal complexes; the replacement of the two chloride ligands by the disulfonimides of the general formulae I to III in the known Grubbs catalysts and Hoveyda-Grubbs catalysts may be mentioned by way of example;

b) In deprotonated form, the disulfonimides having the general formulae I to III are also suitable as chiral anion in asymmetric synthesis.

The present invention further provides for the use of the compounds having the formulae I to III as NMR shift reagents and as reagents for resolution of racemates.

EXPERIMENTAL PART

General Method for the Mukaiyama Aldol Reaction at Room Temperature

Disulfonimide VIIa (0.41 mg, 0.5 mol %) and benzaldehyde (10 µL, 0.1 mmol) together with 0.5 ml of toluene or pentane are placed in a reaction vessel at room temperature. tert-Butyl(1-methoxyvinyloxy)dimethylsilane or tert-butyl (1-isopropoxyvinyloxy)dimethylsilane (0.11 mmol) is added dropwise and the mixture is stirred at room temperature for 1-2 hours.

The solvent is then removed under reduced pressure and 0.05 mmol of $Ph_3CH$ is added as internal standard for an NMR measurement for determining the yield. The mixture is dissolved in about 1 ml of $CDCl_3$, and 0.5-0.75 ml is taken for an NMR measurement. The remaining solution is used for preparative thin layer chromatography. The enantiomeric excess is determined by means of a chiral GC or chiral HPLC measurement on the product isolated from this thin layer chromatography.

Scheme 10: Selection of results achieved using disulfonimide VIa in the Mukaiyama aldol reaction at -78° C.

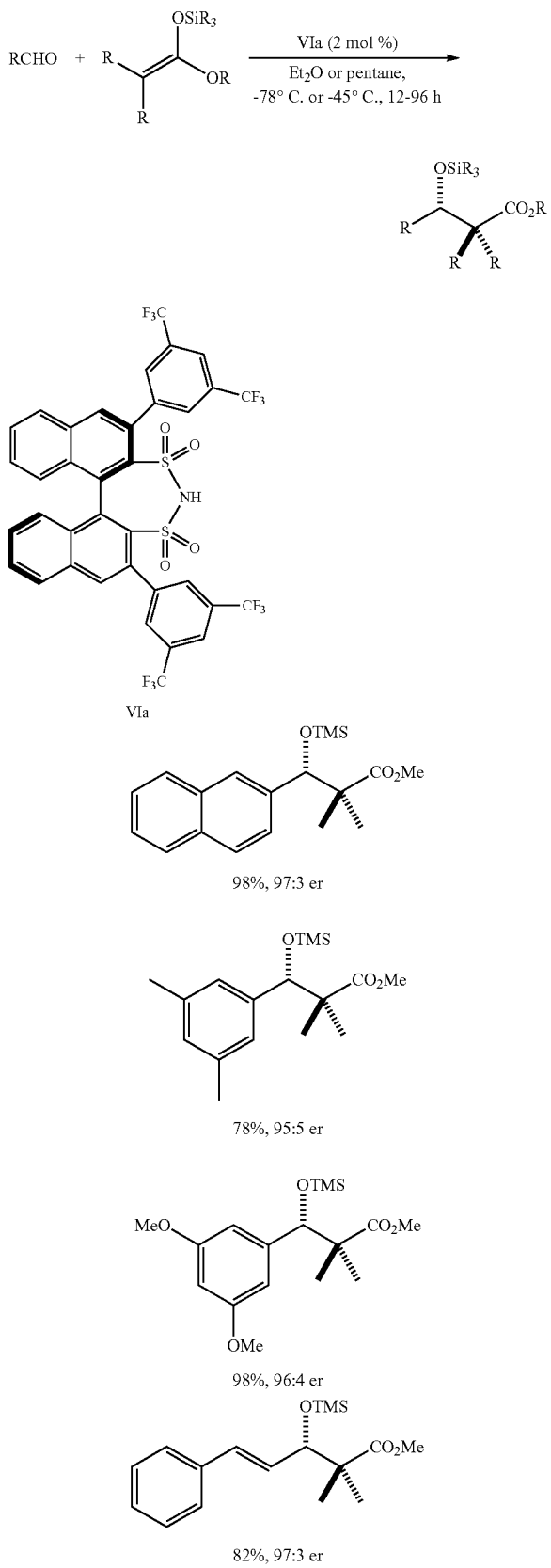

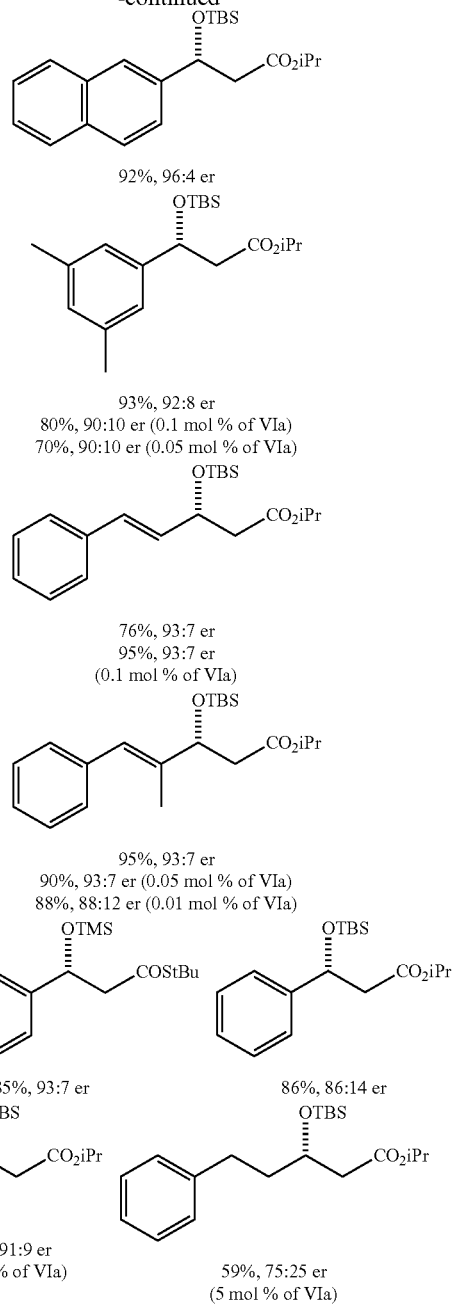

General Synthetic Method for the Vinylic Mukaiyama Aldol Reaction

Disulfonimide VIa (2.05 mg, 5 mol %) and the appropriate aldehyde (0.05 mmol, 1 eq) together with 0.25 ml of $Et_2O$ are placed in a reaction vessel at −78° C. (Z)-tert-Butyl((1-ethoxybuta-1,3-dien-1-yl)oxy)dimethylsilane (0.065 mmol, 1.3 eq) is added dropwise and the mixture is stirred at −78° C. for 72 hours. The mixture is then quenched with saturated $NaHCO_3$ solution (0.25 ml) and diluted with dichloromethane (5 ml). The solution is dried over $Na_2SO_4$. The solvent is then removed under reduced pressure and 0.05 mmol of $Ph_3PH$ is added as internal standard for an NMR measurement to determine the yield. The mixture is dissolved in about 1 ml of $CDCl_3$ and 0.5-0.75 ml is taken for an NMR measurement. The remaining solution is used for preparative thin layer chromatography. The enantiomeric excess is determined by means of a chiral GC or chiral HPLC measurement on the product isolated from this thin layer chromatography.

Scheme 11: Selection of results achieved using disulfonimide VIa in the vinylic Mukaiyama aldol reaction.

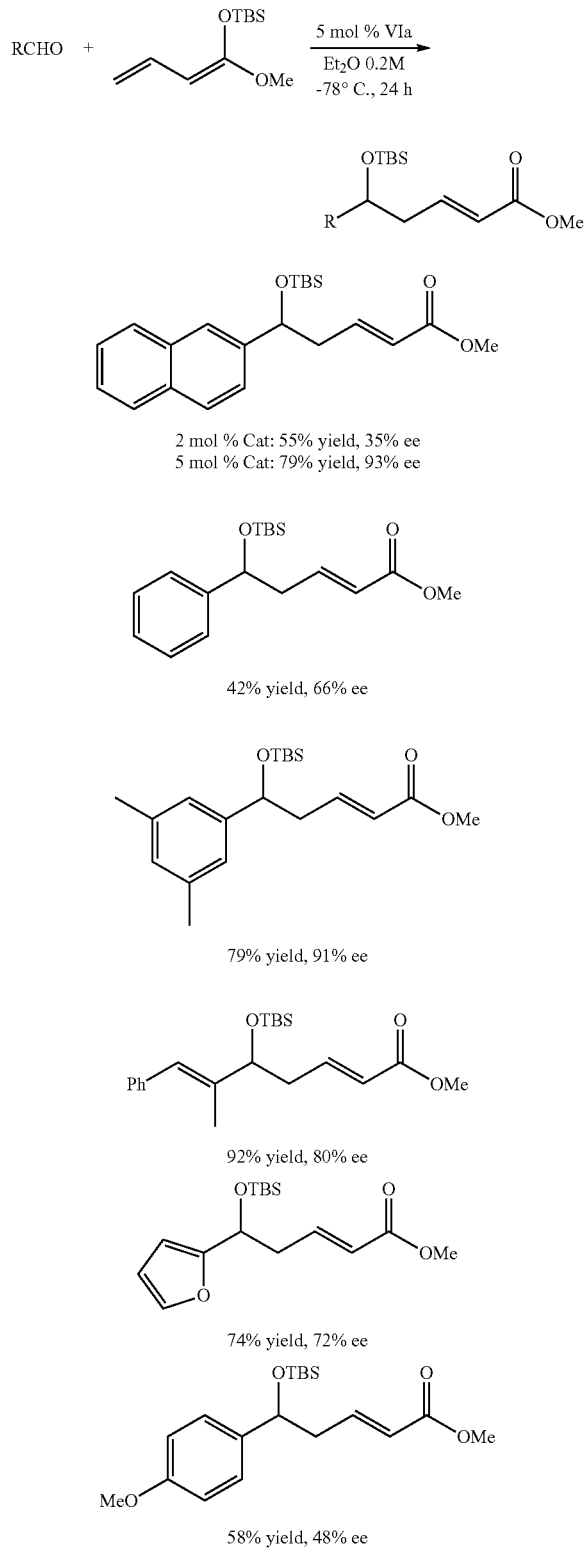

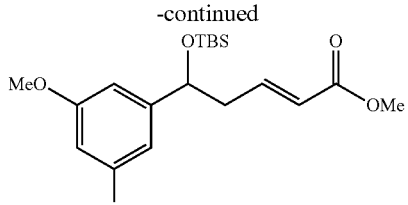

17% yield, 75% ee

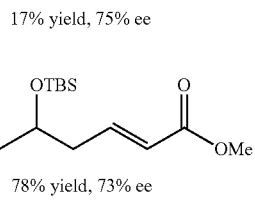

78% yield, 73% ee

General Synthetic Method for the Allylation of Aldehydes

Disulfonimide VIa (2.05 mg, 5 mol %) and the appropriate aldehyde (0.05 mmol, 1 eq) together with 0.25 ml of Et$_2$O are placed in a reaction vessel at −78° C. Trimethyl(2-methylallyl)silane (0.065 mmol, 1.3 eq) is added dropwise and the mixture is stirred at −78° C. for 12-16 hours. The mixture is then quenched with saturated NaHCO$_3$ solution (0.25 ml) and diluted with dichloromethane (5 ml). The solution is dried over Na$_2$SO$_4$. The solvent is then removed under reduced pressure and 0.05 mmol of Ph$_3$PH is added as internal standard for an NMR measurement for determining the yield. The mixture is dissolved in about 1 ml of CDCl$_3$ and 0.5-0.75 ml is taken for an NMR measurement. The remaining solution is used for preparative thin layer chromatography. The enantiomeric excess is determined by means of a chiral GC or chiral HPLC measurement on the product isolated from this thin layer chromatography.

Scheme 12: Selection of results achieved using disulfonimide VIa in the allylation of aldehydes.

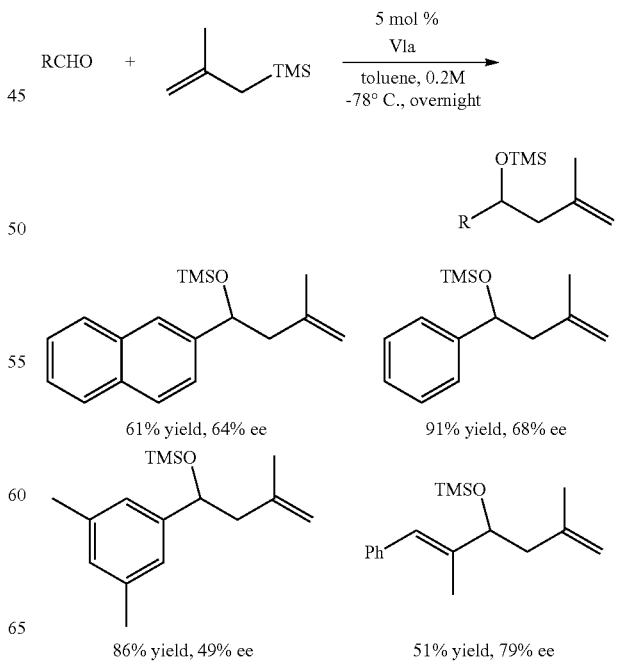

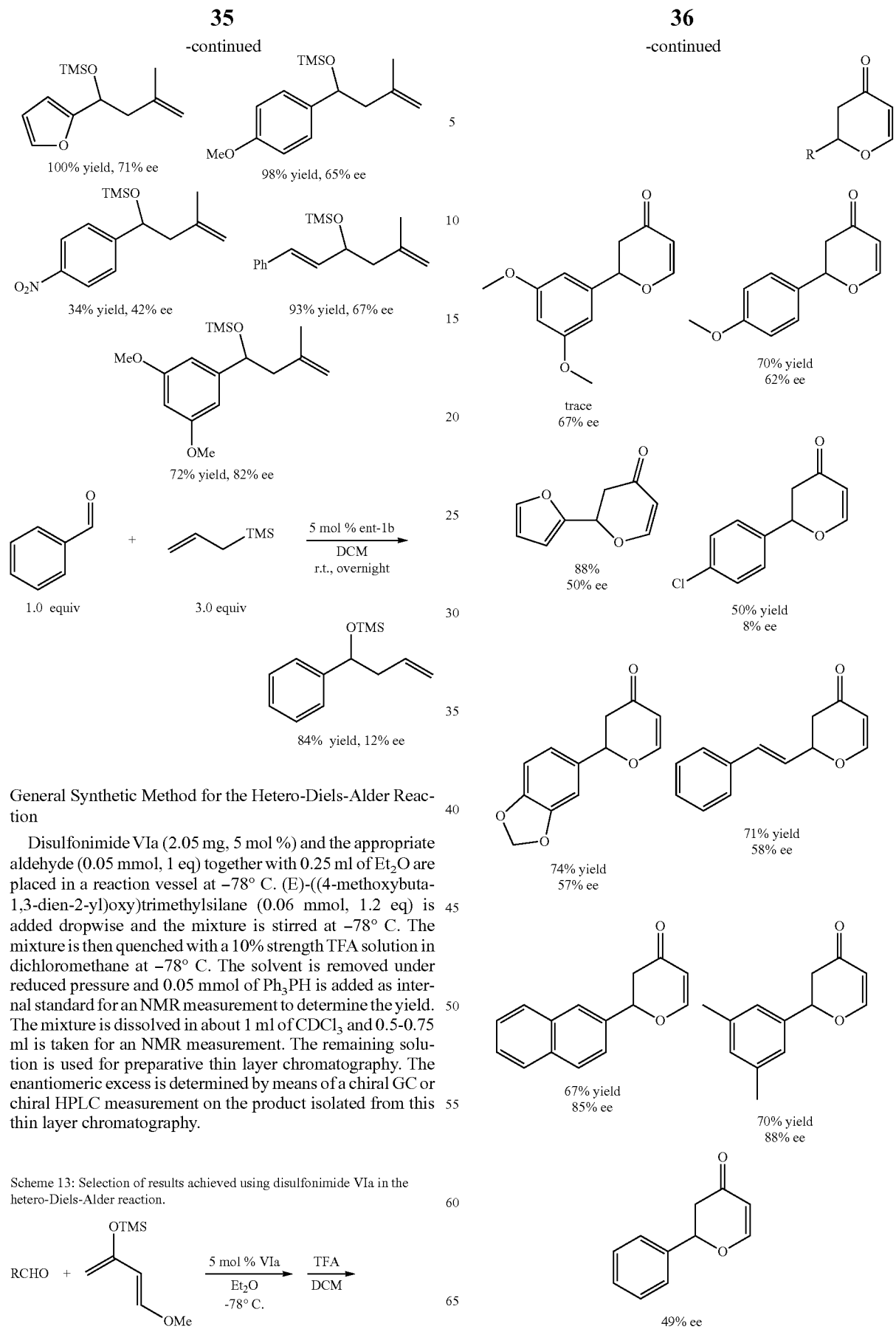

General Synthetic Method for the Hetero-Diels-Alder Reaction

Disulfonimide VIa (2.05 mg, 5 mol %) and the appropriate aldehyde (0.05 mmol, 1 eq) together with 0.25 ml of Et$_2$O are placed in a reaction vessel at −78° C. (E)-((4-methoxybuta-1,3-dien-2-yl)oxy)trimethylsilane (0.06 mmol, 1.2 eq) is added dropwise and the mixture is stirred at −78° C. The mixture is then quenched with a 10% strength TFA solution in dichloromethane at −78° C. The solvent is removed under reduced pressure and 0.05 mmol of Ph$_3$PH is added as internal standard for an NMR measurement to determine the yield. The mixture is dissolved in about 1 ml of CDCl$_3$ and 0.5-0.75 ml is taken for an NMR measurement. The remaining solution is used for preparative thin layer chromatography. The enantiomeric excess is determined by means of a chiral GC or chiral HPLC measurement on the product isolated from this thin layer chromatography.

Scheme 13: Selection of results achieved using disulfonimide VIa in the hetero-Diels-Alder reaction.

General Synthetic Method for TMSCN Addition onto Aldehydes

Disulfonimide VIa (2.05 mg, 5 mol %) and the appropriate aldehyde (0.05 mmol, 1 eq) together with 0.25 ml of $Et_2O$ are placed in a reaction vessel at −25° C. TMSCN (0.15 mmol, 3 eq) is added and the mixture is stirred at −78° C. The mixture is then quenched with 10% strength TFA solution in dichloromethane at −25° C. The solvent is removed under reduced pressure and 0.05 mmol of $Ph_3PH$ is added as internal standard for an NMR measurement to determine the yield. The mixture is dissolved in about 1 ml of $CDCl_3$ and 0.5-0.75 ml is taken for an NMR measurement. The remaining solution is used for preparative thin layer chromatography. The enantiomeric excess is determined by means of a chiral GC or chiral HPLC measurement on the product isolated from this thin layer chromatography.

Scheme 14: Selection of results achieved using disulfonamide VIa in the TMSCN addition reaction.

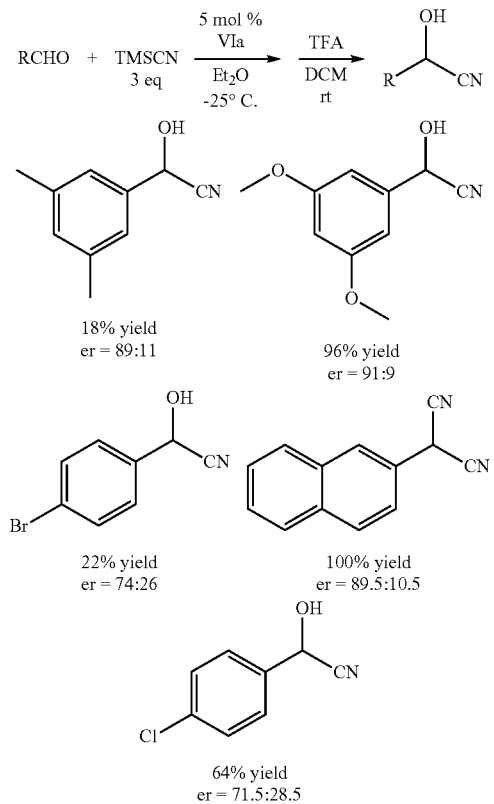

General Method for Preparing the Disulfonimides a) Preparation of the O-arylthiocarbamates XIII and XIV.

The appropriate diol (1 eq) together with DMF (0.2 M) is placed in a reaction vessel at 0° C. or room temperature. 60% strength NaH in oil (4 eq) is added quickly but a little at a time. After stirring at room temperature for 5 minutes, N,N-dimethylthiocarbamoyl chloride in DMF (6 mmol/ml) is added by means of a syringe. The mixture is subsequently heated at 80° C. for 12-18 hours. After cooling, the solution is admixed with 2% strength KOH. The precipitate formed is filtered off with suction, washed with 2% strength KOH, dissolved in dichloromethane and washed with water. The organic phase is dried over $Na_2SO_4$ and evaporated. Column chromatography ($SiO_2$, ethyl acetate/hexane) gives the desired O-arylthiocarbamate.

b) Preparation of the S-arylthiocarbamates XV and XVI

The O-arylthiocarbamate is heated at 250° C. under argon for 80-90 minutes. Purification by column chromatography ($SiO_2$, ethyl acetate/hexane) gives the desired S-arylthiocarbamate.

c) Preparation of the Disulfonic Acids XVI and XVIII

Acetic acid or formic acid (10 times the volume of 30% strength $H_2O_2$) is placed in a reaction vessel at 0° C. or room temperature and 30% strength $H_2O_2$ (30 eq) is added dropwise. After stirring at RT for 1 hour, the S-arylthiocarbamate dissolved in acetic acid, THF or dichloromethane (5 times the volume of 30% strength $H_2O_2$) is added. After stirring at room temperature for 1-72 hours, the solution is evaporated or filtered through silica gel and then evaporated. Column chromatography ($SiO_2$, dichloromethane/methanol) gives the salt of the desired acid. This is converted into the desired acid by washing with 2-6M HCl or by means of ion exchange chromatography.

d) Preparation of the Disulfonic Acid Chlorides XIX and XX

The appropriate disulfonic acid together with thionyl chloride is placed under argon in a reaction vessel. After addition of a catalytic amount of DMF, the mixture is refluxed for 1-4 hours. The thionyl chloride is removed under reduced pressure and the product is purified by digestion with diethyl ether or by column chromatography ($SiO_2$, hexane/ethyl acetate).

d1) Preparation of The Disulfonic Acid Chlorides XIX and XX

The appropriate S-arylthiocarbamate is suspended in a mixture of 2M HCl/acetonitrile (1:5) at 0° C. N-Chlorosuccinimide (4-30 eq) is added a little at a time. After stirring at just under 20° C. for 10-240 minutes, the suspension is extracted with diethyl ether, washed with saturated NaCl solution and evaporated. Purification is carried out by means of column chromatography ($SiO_2$, ethyl acetate/pentane).

e) Preparation of the Disulfonimides IV and V

The appropriate disulfonic acid chloride is dissolved in THF. Ammonia (5-30 eq) in methanol is added a little at a time or via a syringe pump at from −10° C. to 60° C. and the mixture is stirred at this temperature for 6-120 hours. After removal of the solvent, the salt of the disulfonimide is obtained by purification by means of column chromatography ($SiO_2$, hexane/ethyl acetate). This is converted into the desired disulfonimide by washing with 2-6M HCl or by means of ion exchange chromatography.

e1) Preparation of the Disulfonimides IV and V Via the Diboronates XXII and XXIII or the Dihalides XX and XXI The appropriate disulfonimide IVa or Va ($R^1$, $R^{12}$=H or $R^{1'}$, $R^{12'}$=H) is deprotonated by means of n-BuLi, sec-BuLi or tert-BuLi at from −78° C. to 0° C. Addition of a halide source or a boron source at from −78° C. to 0° C. gives the dihalides XX or XXI or diboronates XXII or XXIII. After stirring at room temperature for 1-120 hours, the solution is quenched with ammonium chloride. The aqueous phase is extracted with a suitable organic solvent. The organic phase is dried over $Na_2SO_4$ and evaporated. Column chromatography ($SiO_2$, dichloromethane/methanol) gives the salt of the desired dihalide XX or XXI or diboronate XXII or XXIII. This salt is converted into the desired acid by washing with 2-6M HCl or by means of ion exchange chromatography.

The diiodide is heated with the appropriate boronic acid (2-20 eq) and 1-40 mol % of $Pd(PPh_3)_4$ under argon in a degassed mixture of 2M $Na_2CO_{3aq.}$ (2-30 eq) and DME at 50-150° C. for 1-72 hours. After cooling the reaction mixture, the mixture is diluted with water. The mixture is extracted with ethyl acetate, the organic phases are dried over $Na_2SO_4$ and evaporated. Column chromatography ($SiO_2$, dichloromethane/methanol) gives the salt of the desired disulfonimide IV or V. This salt is converted into the desired acid by washing with 2-6M HCl or by means of ion exchange chromatography.
Scheme 15: Disulfonimides having a chiral BINOL backbone prepared.
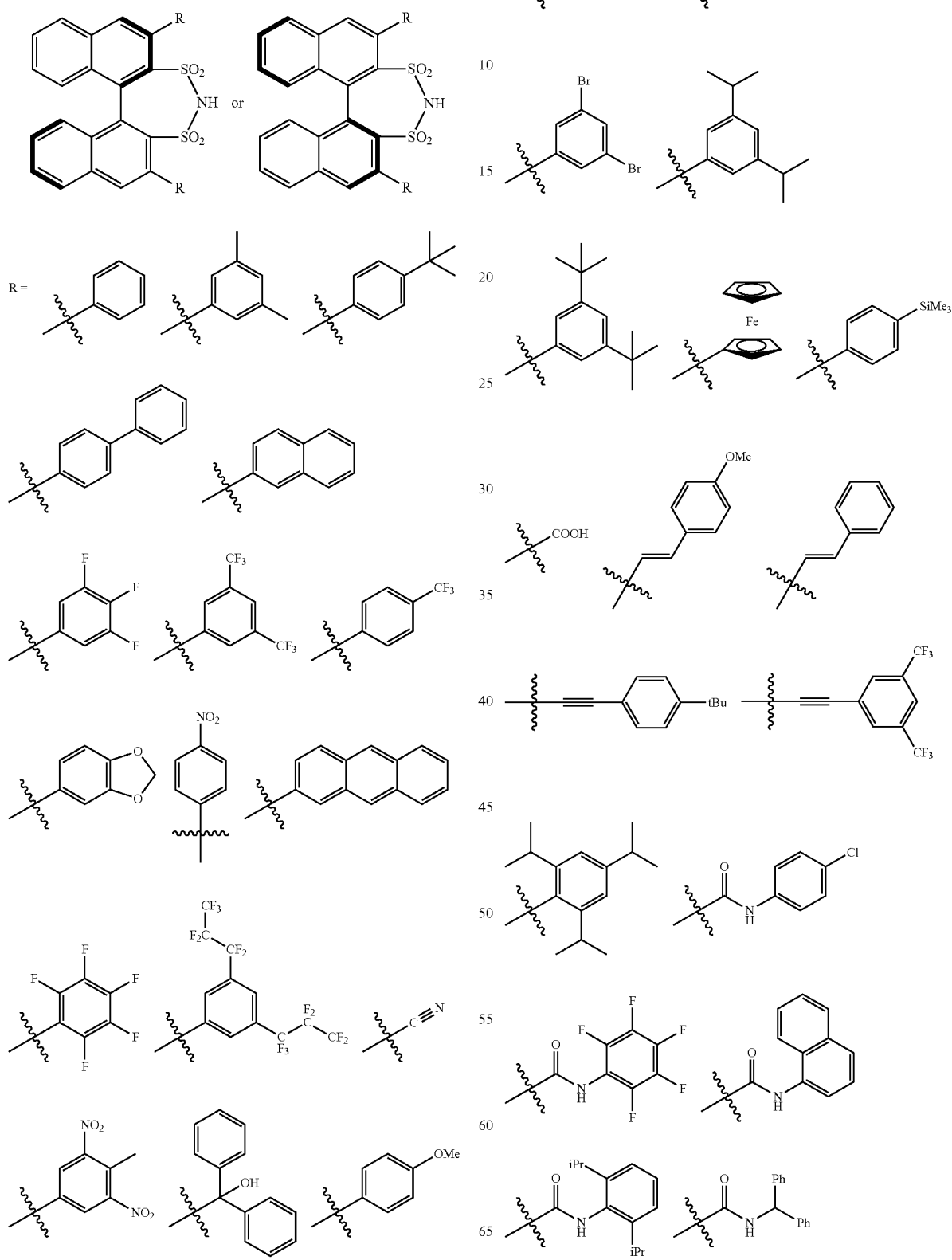

Scheme 16: Disulfonimide having a chiral H8-BINOL backbone prepared.

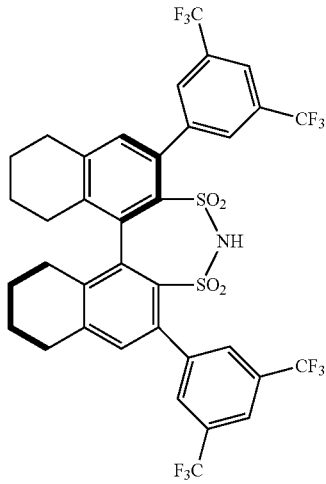

The invention claimed is:

1. A chiral disulfonimide having the formula IV:

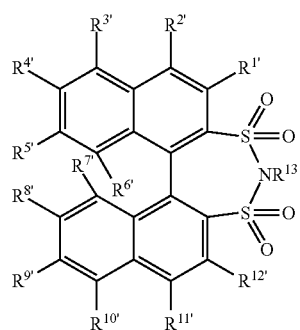

where
$R^{1'}, R^{2'}, R^{3'}, R^{4'}, R^{5'}, R^{6'}, R^{7'}, R^{8'}, R^{9'}, R^{10'}, R^{11'}$ and $R^{12'}$ can be identical or different and each, independently of one another, represent H, OH, F, Cl, Br, I, CN, $NO_2$, NO, $SO_2$, $SO_3H$, $NH_2$, $PH_3$, COOH, $SO_3X$, COOY, where X and Y are each Na or K, a $C_1$-$C_{20}$-alkyl, $C_2$-$C_{20}$-alkenyl or $C_2$-$C_{20}$-alkynyl, aryl, aryl-($C_1$-$C_6$)-alkyl, hetero($C_1$-$C_6$)-alkyl, heteroaryl group, which may optionally be substituted, except that either $R^{1'}$ or $R^{12'}$ or both may additionally independently represent tris-mesitylsilyl or tris-phenylsilyl,
$R^{13}$ is H, F, Cl, Br or I, $C_1$-$C_6$-alkyl, $C_2$-$C_6$-alkenyl or $C_2$-$C_6$-alkynyl, aryl, aryl-($C_1$-$C_6$)-alkyl, hetero($C_1$-$C_6$)-alkyl, heteroaryl, or $SiR^{14}R^{15}R^{16}$, where $R^{14}$, $R^{15}$, $R^{16}$ are each $C_1$-$C_6$-alkyl, $C_2$-$C_6$-alkenyl or $C_2$-$C_6$-alkynyl, aryl, aryl-($C_1$-$C_6$)-alkyl, hetero($C_1$-$C_6$)-alkyl, heteroaryl, which may optionally be substituted,
or an organic salt, metal salt or metal complex thereof.

2. The chiral disulfonimide as claimed in claim 1, wherein at least one of $R^{1'}$ and $R^{12'}$ is not hydrogen and is selected from among phenyl-, 2,4,6-triisopropylphenyl, mesityl, 9-phenanthryl, 9-anthracenyl, 1-naphthyl, 2-naphthyl, 4-biphenyl, 3,5-(trifluoromethyl)phenyl, 2,6-dimethylphenyl, tert-butyl, tris-mesitylsilyl, tris-phenylsilyl, 4-nitrophenyl and 2,6-methyl-4-butylphenyl, trifluoromethyl, 3,4,5-trifluorophenyl, and/or pentafluorophenyl.

3. The chiral disulfonimide as claimed in claim 1, wherein that at least one of the radicals $R^{4'}$ and $R^{9'}$ is selected from among $NO_2$ and I.

4. The chiral disulfonimide as claimed in claim 1, wherein $R^{13}$ is H, F, Cl, Br, I or $SiR^{14}R^{15}R^{16}$, where $R^{14}$, $R^{15}$, $R^{16}$ are each $C_1$-$C_6$-alkyl, $C_2$-$C_6$-alkenyl or $C_2$-$C_6$-alkynyl.

5. The chiral disulfonimide as claimed in claim 4, wherein $R^{13}$ is $SiR^{14}R^{15}R^{16}$.

6. A process for preparing a chiral disulfonimide having the formula IV as claimed in claim 1,
said process comprising the following steps:
(A) reacting a Binol derivative having the formula X:

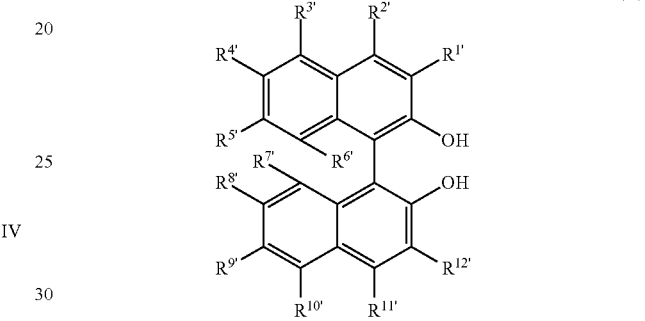

with a thiocarbamoyl chloride of the formula XII:

where the radicals $R^{1'}$, $R^{2'}$, $R^{3'}$, $R^{4'}$, $R^{5'}$, $R^{6'}$, $R^{7'}$, $R^{8'}$, $R^{9'}$, $R^{10'}$, $R^{11'}$ and $R^{12'}$ are defined as in claim 1, and
where $R^{17}$ and $R^{18}$ can be identical or different and are each a $C_1$-$C_6$-alkyl group, to form an O-arylthiocarbamate having the formula XIII,

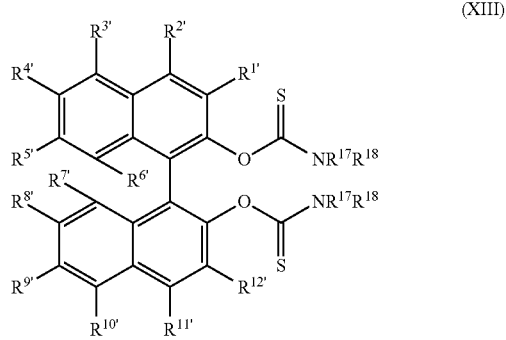

(B) converting the O-arylthiocarbamate having the formula XIII into the corresponding S-arylthiocarbamate having the formula XV, (A) reacting a Binol derivative having the formula X:

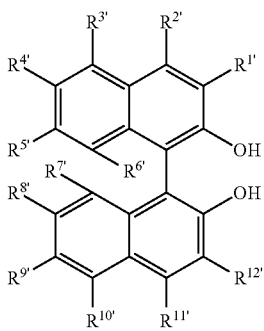
(X)

with a thiocarbamoyl chloride of the formula XII:

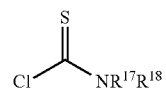
(XII)

where the radicals $R^{1'}$, $R^{2'}$, $R^{3'}$, $R^{4'}$, $R^{5'}$, $R^{6'}$, $R^{7'}$, $R^{8'}$, $R^{9'}$, $R^{10'}$, $R^{11'}$ and $R^{12'}$ are defined as in claim 1, and where $R^{17}$ and $R^{18}$ can be identical or different and are each a $C_1$-$C_6$-alkyl group, to form an O-arylthiocarbamate having the formula XIII,

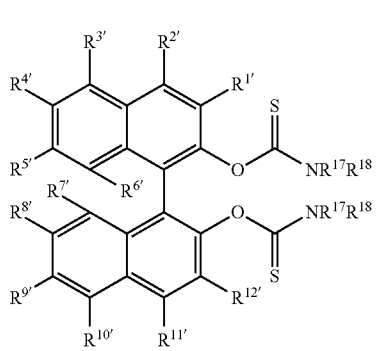
(XIII)

(B) converting the O-arylthiocarbamate having the formula XIII into the corresponding S-arylthiocarbamate having the formula XV,

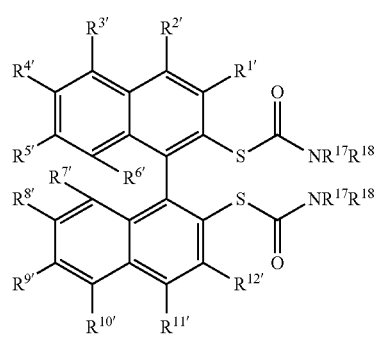
(XV)

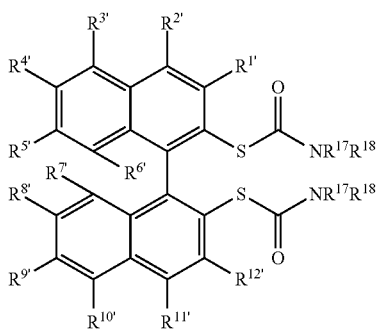
(XV)

and (C) converting the S-arylthiocarbamate in the presence of an oxidant into the compound having the formula XVII,

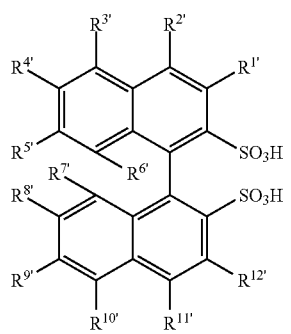
(XVII)

(D) converting the sulfonic acid obtained in step C into the acid halide having the formula XIX,

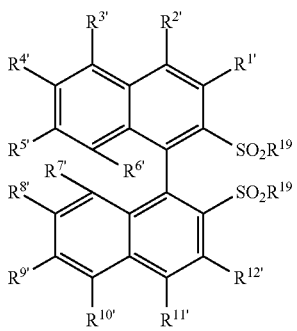
(XIX)

where $R^{19}$=Cl, and in a subsequent process step (E) converting the acid halide having the formula XIX by means of ammonia or a primary amine into the corresponding imide having the formula IV.

7. A process for preparing a chiral disulfonimide having the formula IV as claimed in claim 1, said process comprising the following steps:

and (C) converting the S-arylthiocarbamate having the formula XV directly into the compound having the formula XIX,

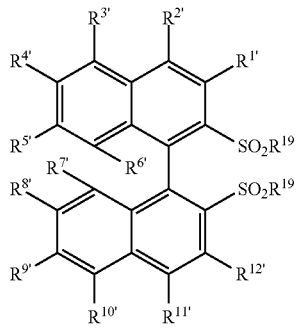
(XIX)

where $R^{19}$=Cl.

8. A process for preparing a compound having the formulae IV as claimed in claim 1 or an organic salt, metal salt or metal complex thereof:

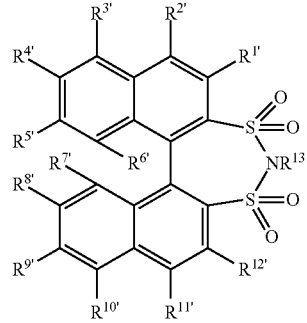
(IV)

where $R^{1'}$, $R^{2'}$, $R^{3'}$, $R^{4'}$, $R^{5'}$, $R^{6'}$, $R^{7'}$, $R^{8'}$, $R^{9'}$, $R^{10'}$, $R^{11'}$, $R^{12'}$ and $R^{13}$ are as defined in claim 1, said process comprising the following steps:

F) converting a 3,3'-unsubstituted disulfonimide having the formula IVa

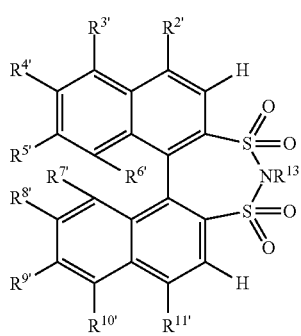
(IVa)

into a 3,3'-dihalide or a 3,3'-ditriflate having the formula XX

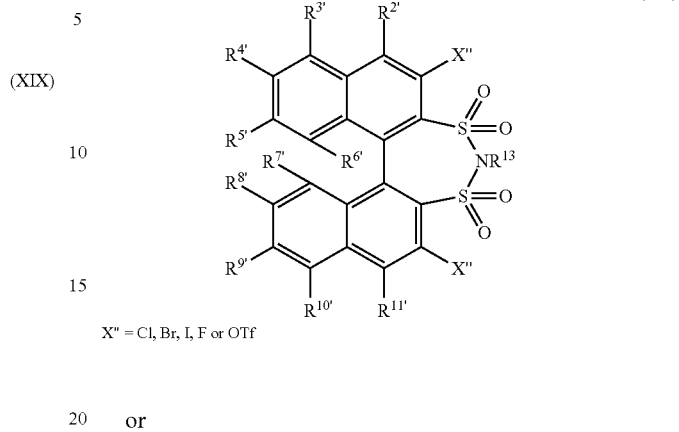
(XX)

X" = Cl, Br, I, F or OTf or

G) converting a disulfonimide IVa into a 3,3'-diboronate having the formula XXII

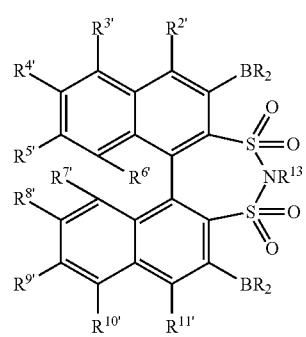
(XXII)

where the radicals $BR^2$ in XXII can be identical or different and are each $B(OH)_2$, $B(alkyl)_2$, $B(Oalkyl)_2$, $B(pinacol)$, $BF_3X'$, where $X'$=Na, K, and H) in a further process step, converting a compound having the formulae XX or XXII by means of a coupling reaction into the imide having the formula IV.

9. Method of conducting a chemical reaction, comprising reacting reactants in the presence of a chiral Brønsted acid catalyst or a chiral Lewis acid catalyst, wherein the chiral Brønsted acid catalyst or the chiral Lewis acid catalyst is a compound having the formula IV as claimed in claim 1

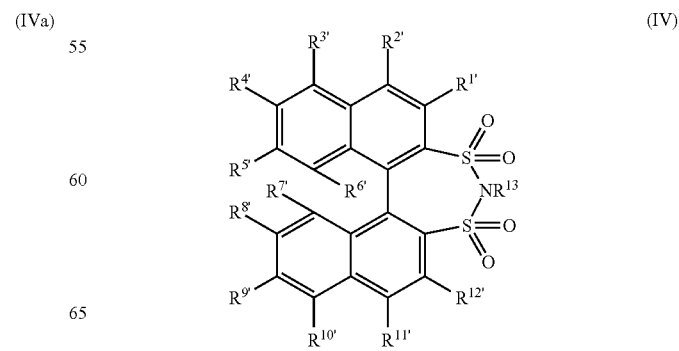
(IV)

where
R$^{1'}$, R$^{2'}$, R$^{3'}$, R$^{4'}$, R$^{5'}$, R$^{6'}$, R$^{7'}$, R$^{8'}$, R$^{9'}$, R$^{10'}$, R$^{11'}$ and R$^{12'}$, can be identical or different and are each, independently of one another, H, OH, F, Cl, Br, I, CN, NO$_2$, NO, SO$_2$, SO$_3$H, NH$_2$, PH$_3$, COOH, SO$_3$X, COOY, where X and Y are each Na or K, a C$_1$-C$_{20}$-alkyl, C$_2$-C$_{20}$-alkenyl or C$_2$-C$_{20}$-alkynyl, aryl, aryl-(C$_1$-C$_6$)-alkyl, hetero(C$_1$-C$_6$)-alkyl, heteroaryl group, which may optionally be substituted, R$^{13}$ is H, F, Cl, Br, I or SiR$^{14}$R$^{15}$R$^{16}$, where R$^{14}$, R$^{15}$, R$^{16}$ are each C$_1$-C$_6$-alkyl, C$_2$-C$_6$-alkenyl or C$_2$-C$_6$-alkynyl, aryl, aryl-(C$_1$-C$_6$)-alkyl, hetero(C$_1$-C$_6$)-alkyl, heteroaryl, which may optionally be substituted, or a salt or metal complex thereof.

10. Method as claimed in claim 8, wherein R$^{13}$ is SiR$^{14}$R$^{15}$R$^{16}$.

11. Method comprising conducting an NMR shift in the presence of an NMR shift reagent, or comprising resolving a racemic mixture with the aid of a resolution reagent, wherein the NMR shift reagent or the resolution reagent is a compound having the formula IV as claimed in claim 1.

12. Method of conducting a chemical reaction comprising activation of at least one chemical selected from the group consisting of ketones, aldehydes and alkenes in the presence of a chiral Brønsted acid catalyst or a chiral Lewis acid catalyst, wherein the chiral Brønsted acid catalyst or the chiral Lewis acid catalyst is a compound having the formula IV as claimed in claim 1.

13. Method of conducting a chemical reaction comprising reacting reactants in the presence of at least one catalyst, wherein the catalyst is a compound having the formula IV as claimed in claim 1, and wherein the chemical reaction is selected from the group consisting of aldol reactions, Mukaiyama aldol reactions, Mukaiyama-Michael reactions, Michael additions, Mannich reactions, esterifications, etherifications, pinacol rearrangements, as acetalizations and related reactions, cycloadditions, hydroaminations, hydroalkoxylation, hydrations, olefin activations, Friedel-Crafts reactions, epoxide openings, Ritter reactions, nucleophilic substitutions of alcohols, asymmetric ring openings, transfer hydrogenations, alkyne additions, allylations, epoxidations, olefin metathesis, isomerizations, iminium catalysis and enamine catalysis.

14. A chiral disulfonimide having the formula V:

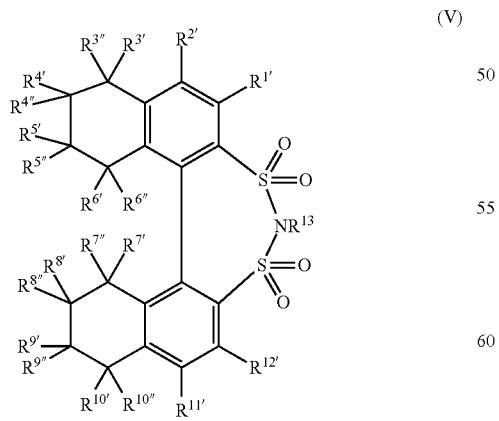

(V)

where
R$^{1'}$, R$^{2'}$, R$^{3'}$, R$^{4'}$, R$^{5'}$, R$^{6'}$, R$^{7'}$, R$^{8'}$, R$^{9'}$, R$^{10'}$, R$^{11'}$, R$^{12'}$, R$^{3''}$, R$^{4''}$, R$^{5''}$, R$^{6''}$, R$^{7''}$, R$^{8''}$, R$^{9''}$ and R$^{10''}$ can be identical or different and each, independently of one another, represent H, OH, F, Cl, Br, I, CN, NO$_2$, NO, SO$_2$, SO$_3$H, NH$_2$, PH$_3$, COOH, SO$_3$X, COOY, where X and Y are each Na or K, a C$_1$-C$_{20}$-alkyl, C$_2$-C$_{20}$-alkenyl or C$_2$-C$_{20}$-alkynyl, aryl, aryl-(C$_1$-C$_6$)-alkyl, hetero(C$_1$-C$_6$)-alkyl, heteroaryl group, which may optionally be substituted, except that either R$^{1'}$ or R$^{12'}$ or both may additionally independently represent tris-mesitylsilyl or tris-phenylsilyl, R$^{13}$ is H, F, Cl, Br or I, C$_1$-C$_6$-alkyl, C$_2$-C$_6$-alkenyl or C$_2$-C$_6$-alkynyl, aryl, aryl-(C$_1$-C$_6$)-alkyl, hetero(C$_1$-C$_6$)-alkyl, heteroaryl, or SiR$^{14}$R$^{15}$R$^{16}$, where R$^{14}$, R$^{15}$, R$^{16}$ are each C$_1$-C$_6$-alkyl, C$_2$-C$_6$-alkenyl or C$_2$-C$_6$-alkynyl, aryl, aryl-(C$_1$-C$_6$)-alkyl, hetero(C$_1$-C$_6$)-alkyl, heteroaryl, which may optionally be substituted, or an organic salt, metal salt or metal complex thereof.

15. The chiral disulfonimide as claimed in claim 14, wherein at least one of R$^{1'}$ and R$^{12'}$ is not hydrogen and is selected from among phenyl-, 2,4,6-triisopropylphenyl, mesityl, 9-phenanthryl, 9-anthracenyl, 1-naphthyl, 2-naphthyl, 4-biphenyl, 3,5-(trifluoromethyl)phenyl, 2,6-dimethylphenyl, tert-butyl, tris-phenylsilyl, 4-nitrophenyl and 2,6-methyl-4-butylphenyl, trifluoromethyl, 3,4,5-trifluorophenyl, and/or pentafluorophenyl.

16. The chiral disulfonimide as claimed in claim 14, wherein that at least one of the radicals R$^{4'}$ and R$^{9'}$ or R$^{4''}$ and R$^{9''}$ is selected from among NO$_2$ and I.

17. The chiral disulfonimide as claimed in claim 14, wherein R$^{13}$ is H, F, Cl, Br, I or SiR$^{14}$R$^{15}$R$^{16}$, where R$^{14}$, R$^{15}$, R$^{16}$ are each C$_1$-C$_6$-alkyl, C$_2$-C$_6$-alkenyl or C$_2$-C$_6$-alkynyl.

18. The chiral disulfonimide as claimed in claim 17, wherein R$^{13}$ is SiR$^{14}$R$^{15}$R$^{16}$.

19. A process for preparing a chiral disulfonimide having the formula V as claimed in claim 14,
said process comprising the following steps:
(A) reacting an H8-Binol derivative having the formula XI:

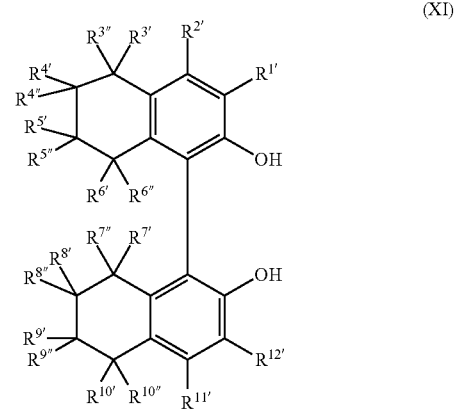

(XI)

with a thiocarbamoyl chloride of the formula XII:

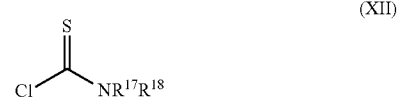

(XII)

where the radicals R$^{1'}$, R$^{2'}$, R$^{3'}$, R$^{4'}$, R$^{5'}$, R$^{6'}$, R$^{7'}$, R$^{8'}$, R$^{9'}$, R$^{10'}$, R$^{11'}$, R$^{12'}$, R$^{3''}$, R$^{4''}$, R$^{5''}$, R$^{6''}$, R$^{7''}$, R$^{8''}$, R$^{9''}$, and R$^{10''}$ are defined as in claim 14, and where $R^{17}$ and $R^{18}$ can be identical or different and are each a $C_1$-$C_6$-alkyl group, to form an O-arylthiocarbamate having the formula XIV,

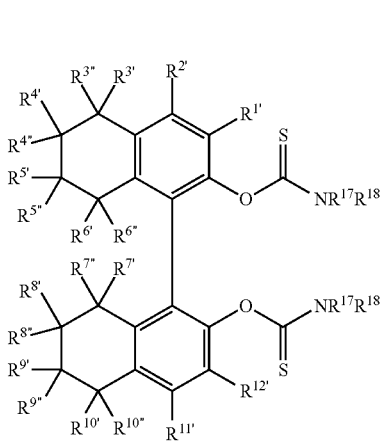

(XIV)

(B) converting the O-arylthiocarbamate having the formula XIV into the corresponding S-arylthiocarbamate having the formula XVI,

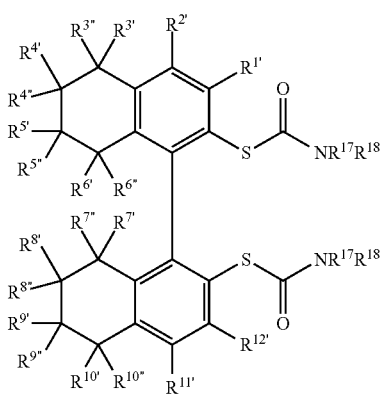

(XVI)

and (C) converting the S-arylthiocarbamate in the presence of an oxidant into the compound having the formula XVIII,

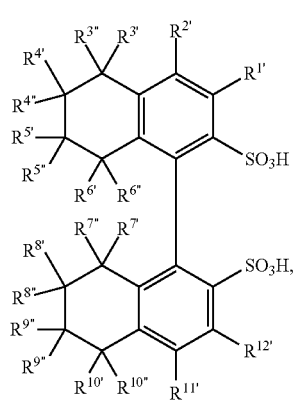

(XVIII)

D) converting the sulfonic acid obtained in step C into the acid halide having the formula XX,

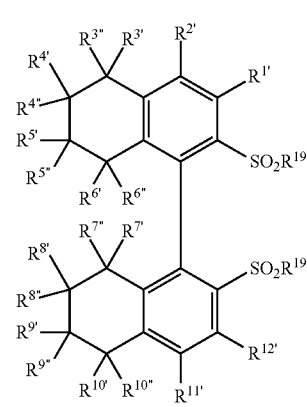

(XX)

where $R^{19}$=Cl, Br, I or F, and in a subsequent process step (E) converting the acid halide having the formula XX by means of ammonia or a primary amine into the corresponding imide having the formula V.

20. A process for preparing a chiral disulfonimide having the formula V as claimed in claim 14, said process comprising the following steps:

(A) reacting an H8-Binol derivative having the formula XI:

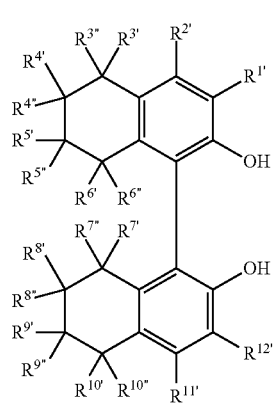

(XI)

with a thiocarbamoyl chloride of the formula XII:

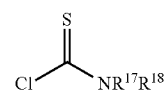

(XII)

where the radicals $R^{1'}$, $R^{2'}$, $R^{3'}$, $R^{4'}$, $R^{5'}$, $R^{6'}$, $R^{7'}$, $R^{8'}$, $R^{9'}$, $R^{10'}$, $R^{11'}$, $R^{12'}$, $R^{3''}$, $R^{4''}$, $R^{5''}$, $R^{6''}$, $R^{7''}$, $R^{8''}$, $R^{9''}$, and $R^{10''}$ are defined as in claim 14, and where $R^{17}$ and $R^{18}$ can be identical or different and are each a $C_1$-$C_6$-alkyl group, to form an O-arylthiocarbamate having the formula XIV,

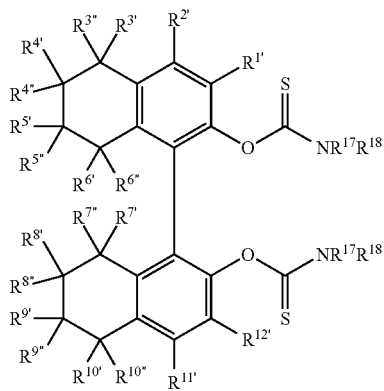

(XIV)

(B) converting the O-arylthiocarbamate having the formula XIV into the corresponding S-arylthiocarbamate having the formula XVI,

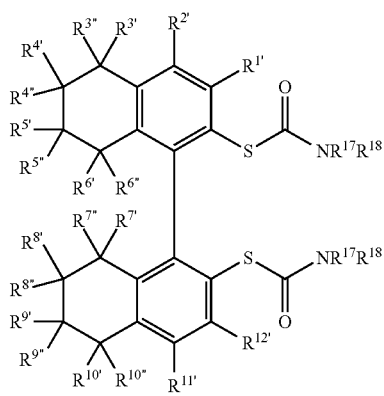

(XVI)

and (C) converting the S-arylthiocarbamate having the formula XVI directly into the compound having the formula XX,

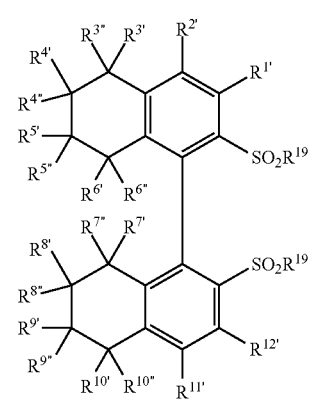

(XX)

where $R^{19}$=Cl, Br, I or F.

21. A process for preparing a compound having the formulae V as claimed in claim 14 or an organic salt, metal salt or metal complex thereof:

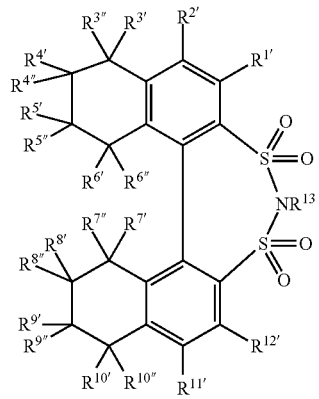

(V)

where $R^{1'}, R^{2'}, R^{3'}, R^{4'}, R^{5'}, R^{6'}, R^{7'}, R^{8'}, R^{9'}, R^{10'}, R^{11'}, R^{12'}, R^{3''}, R^{4''}, R^{5''}, R^{6''}, R^{7''}, R^{8''}, R^{9''}, R^{10''}$, and $R^{13}$ are as defined in claim 14, said process comprising the following steps:

F) converting a 3,3'-unsubstituted disulfonimide having the formula Va

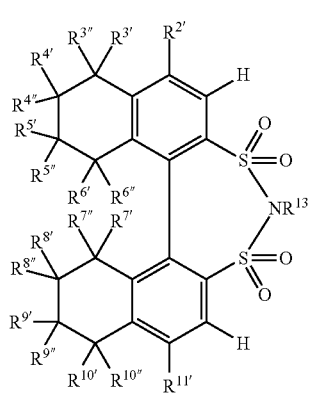

(Va)

into a 3,3'-dihalide or a 3,3'-ditriflate having the formula XXI

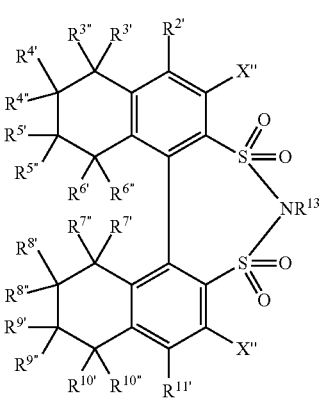

(XXI)

X" = Cl, Br, I, F, or OTf or

G) converting a disulfonimide Va into a 3,3'-diboronate having the formula XXIII

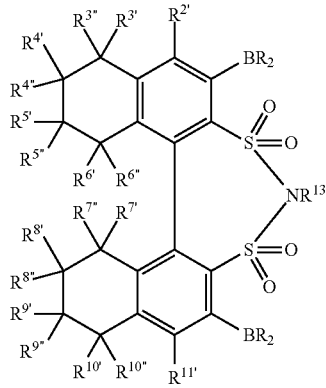
(XXIII)

where the radicals $BR^2$ in XXIII can be identical or different and are each $B(OH)_2$, $B(alkyl)_2$, $B(Oalkyl)_2$, B(pinacol), $BF_3X$, where X=Na, K, and H) in a further process step, converting a compound having the formulae XXII and XXIII by means of a coupling reaction into the imide having the formula V.

22. A process for preparing a compound having the formula V as claimed in claim 14 or an organic salt, metal salt or metal complex thereof

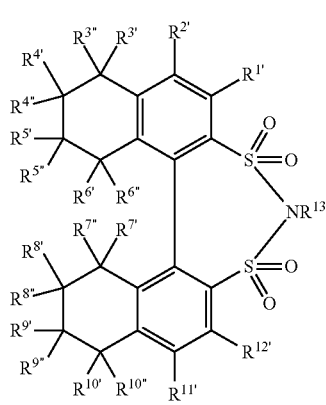
(V)

where $R^{1'}$, $R^{2'}$, $R^{3'}$, $R^{4'}$, $R^{5'}$, $R^{6'}$, $R^{7'}$, $R^{8'}$, $R^{9'}$, $R^{10'}$, $R^{11'}$, $R^{12'}$, $R^{3''}$, $R^{4''}$, $R^{5''}$, $R^{6''}$, $R^{7''}$, $R^{8''}$, $R^{9''}$, and $R^{10''}$ and $R^{13}$ are as defined in claim 14, said process comprising carrying out a directing ortho-metallization to form metal species of the compound V in situ, in which $R^{1'}$, $R^{12'}$=Li, Mg, Zn, Cu, and reacting said metal species with a suitable electrophile selected from the group consisting of $CO_2$, perfluoroalkyl iodides, perfluoroalkyl isocyanates, aldehydes and ketones.

23. Method of conducting a chemical reaction, comprising reacting reactants in the presence of a chiral Brønsted acid catalyst or a chiral Lewis acid catalyst, wherein the chiral Brønsted acid catalyst or the chiral Lewis acid catalyst is a compound having the formula V as claimed in claim 14

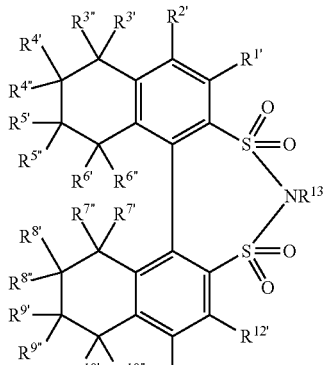
(V)

where
$R^{1'}$, $R^{2'}$, $R^{3'}$, $R^{4'}$, $R^{5'}$, $R^{6'}$, $R^{7'}$, $R^{8'}$, $R^{9'}$, $R^{10'}$, $R^{11'}$, $R^{12'}$, $R^{3''}$, $R^{4''}$, $R^{5''}$, $R^{6''}$, $R^{7''}$, $R^{8''}$, $R^{9''}$, and $R^{10''}$ can be identical or different and are each, independently of one another, H, OH, F, Cl, Br, I, CN, $NO_2$, NO, $SO_2$, $SO_3H$, $NH_2$, $PH_3$, COOH, $SO_3X$, COOY, where X and Y are each Na or K, a $C_1$-$C_{20}$-alkyl, $C_2$-$C_{20}$-alkenyl or $C_2$-$C_{20}$-alkynyl, aryl, aryl-($C_1$-$C_6$)-alkyl, hetero($C_1$-$C_6$)-alkyl, heteroaryl group, which may optionally be substituted, $R^{13}$ is H, F, Cl, Br, I or $SiR^{14}R^{15}R^{16}$, where $R^{14}$, $R^{15}$, $R^{16}$ are each $C_1$-$C_6$-alkyl, $C_2$-$C_6$-alkenyl or $C_2$-$C_6$-alkynyl, aryl, aryl-($C_1$-$C_6$)-alkyl, hetero($C_1$-$C_6$)-alkyl, heteroaryl, which may optionally be substituted, or a salt or metal complex thereof.

24. Method as claimed in claim 21, wherein $R^{13}$ is $SiR^{14}R^{15}R^{16}$.

25. Method comprising conducting an NMR shift in the presence of an NMR shift reagent, or comprising resolving a racemic mixture with the aid of a resolution reagent, wherein the NMR shift reagent or the resolution reagent is a compound having the formula V as claimed in claim 14.

26. Method of conducting a chemical reaction comprising activation of at least one chemical selected from the group consisting of ketones, aldehydes and alkenes in the presence of a chiral Brønsted acid catalyst or a chiral Lewis acid catalyst, wherein the chiral Brønsted acid catalyst or the chiral Lewis acid catalyst is a compound having the formula V as claimed in claim 14.

27. Method of conducting a chemical reaction comprising reacting reactants in the presence of at least one catalyst, wherein the catalyst is a compound having the formula V as claimed in claim 14, and wherein the chemical reaction is selected from the group consisting of aldol reactions, vinylic aldol reactions, Mukaiyama aldol reactions, vinylic Mukaiyama aldol reactions, Mukaiyama-Michael reactions, Michael additions, Mannich reactions, TMSCN additions onto aldehydes and ketones, esterifications, etherifications, pinacol rearrangements, as acetalizations and related reactions, cycloadditions, hydroaminations, hydroalkoxylation, hydrations, olefin activations, Friedel-Crafts reactions, epoxide openings, Ritter reactions, nucleophilic substitutions of alcohols, asymmetric ring openings, asymmetric reductions, transfer hydrogenations, alkyne additions, allylations, epoxidations, olefin metathesis, isomerizations, iminium catalysis and enamine catalysis.

* * * * *